US011174482B2

(12) United States Patent
Alcendor et al.

(10) Patent No.: US 11,174,482 B2
(45) Date of Patent: Nov. 16, 2021

(54) ANTIVIRAL AGENTS

(71) Applicant: Meharry Medical College, Nashville, TN (US)

(72) Inventors: Donald J. Alcendor, Hermitage, TN (US); Waldemar Popik, Brentwood, TN (US)

(*) Notice: Subject to any disclaimer, the term of this patent is extended or adjusted under 35 U.S.C. 154(b) by 0 days.

(21) Appl. No.: 16/436,696

(22) Filed: Jun. 10, 2019

(65) Prior Publication Data

US 2019/0309298 A1    Oct. 10, 2019

Related U.S. Application Data

(63) Continuation of application No. PCT/US2017/066270, filed on Dec. 14, 2017.

(60) Provisional application No. 62/434,802, filed on Dec. 15, 2016, provisional application No. 62/560,144, filed on Sep. 18, 2016.

(51) Int. Cl.
| | |
|---|---|
| *C12N 15/113* | (2010.01) |
| *A61P 31/14* | (2006.01) |
| *A61K 47/59* | (2017.01) |
| *C07F 9/6558* | (2006.01) |

(52) U.S. Cl.
CPC ........ *C12N 15/1131* (2013.01); *A61K 47/593* (2017.08); *A61K 47/595* (2017.08); *A61P 31/14* (2018.01); *C07F 9/65583* (2013.01); *C12N 2310/11* (2013.01); *C12N 2310/314* (2013.01); *C12N 2310/3233* (2013.01); *C12N 2310/346* (2013.01); *C12N 2310/351* (2013.01); *C12N 2320/32* (2013.01)

(58) Field of Classification Search
CPC ............ C12N 15/1131; C12N 2320/32; C12N 2310/11; C12N 2310/314; C12N 2310/3233; C12N 2310/346; C12N 2310/351; C12N 2770/24111; C12N 2310/3515; A61K 47/595; A61K 47/593; C07F 9/65583; A61P 31/14
See application file for complete search history.

(56) References Cited

U.S. PATENT DOCUMENTS

| | | |
|---|---|---|
| 6,610,539 B1 | 8/2003 | Wright et al. |
| 7,285,658 B2 | 10/2007 | Cook et al. |
| 7,807,801 B2 | 10/2010 | Iverson et al. |
| 8,642,752 B2 | 2/2014 | Swayze et al. |
| 8,993,318 B2 | 3/2015 | Bass et al. |
| 9,161,948 B2 | 10/2015 | Hanson |
| 2005/0171044 A1 | 8/2005 | Stein et al. |
| 2008/0161324 A1 | 7/2008 | Johansen et al. |
| 2010/0009970 A1 | 1/2010 | Johansen et al. |
| 2012/0035136 A1 | 2/2012 | Iverson et al. |
| 2016/0074346 A1 | 3/2016 | Fraser et al. |
| 2016/0201148 A1 | 3/2016 | Patel et al. |

FOREIGN PATENT DOCUMENTS

WO    2007032794    3/2007

OTHER PUBLICATIONS

Tabata, T. et al., Zika Virus Targets Different Primary Human Placental Cells, Suggesting Two Routes for Vertical Transmission., Cell Host Microbe, 2016, p. 155-166, vol. 20, No. 2.
International Search Report and Written Opinion of International Searching Authority of International Application No. PCT/US2017/066270, dated Mar. 1, 2018.
Heald, A. et al., AVI-7288 for Marburg Virus in Nonhuman Primates and Humans, The New England Journal of Medicine, 2015, p. 339-348, vol. 373, No. 4.
Stein, D. et al., Nucleic acid-based inhibition of flavivirus infections, Frontiers in Bioscience, 2008, p. 1385-1395, vol. 13.
Lanciotti, R. et al., Phylogeny of Zika Virus in Western Hemisphere, 2016, Emerging Infectious Diseases, p. 933-935, vol. 5, No. 5.
Thomas, D. et al., Local Transmission of Zika Virus—Puerto Rico, Nov. 23, 2015-Jan. 28, 2016, Morbidity and Motality Weekly Report, 2016, p. 154-158, vol. 65.
Dirlikov E. et al., Update: Ongoing Zika Virus Transmission—Puerto Rico, November 1, 2015-Apr. 14, 2016. Morbidity and Motality Weekly Report, 2016, p. 451-455, vol. 65.
Xu, M. et al., Detection of Zika virus by SYBR green one-step real-time RT-PCR., Journal of Virological Methods, 2016, p. 93-97, vol. 236.
Wilkerson, I. et al., Retinal pericytes and cytomegalovirus infectivity: implications for HCMV-induced retinopathy and congenital ocular disease, Journal of Neuroinflammation, 2015; p. 2, vol. 12, No. 1.
Alcendor, D., Zika Virus Infection of the Human Glomerular Cells: Implications for Viral Reservoirs and Renal Pathogenesis, Journal of Infectious Diseases, 2017, p. 162-171, vol. 216.
Khatua, A. et al,. Non-productive HIV-1 infection of human glomerular and urinary podocytes, Virology, 2010, p. 119-127, vol. 408.
Lanciotti, R. et al., Genetic and serologic properties of Zika virus associated with an epidemic, Yap State, Micronesia, 2007, Emerging Infectious Diseases, 2008; p. 1232-1239, vol. 14, No. 8.
Moulton, J. et al., Using morpholines to control gene expression, Current Protocols in Nucleic Acid Chemistry, 2017, p. 4.301.1-4.30.29, vol. 68, No. 1.

(Continued)

*Primary Examiner* — J. E. Angell
(74) *Attorney, Agent, or Firm* — Bradley Arant Boult Cummings; Timothy L. Capria; Alexandra C. Lynn

(57) ABSTRACT

An antiviral agent is provided, having a phosphorodiamidate morpholino oligomer with an antisense sequence to a portion of a genome of a strain of Zika virus (ZIKV). The antiviral agent finds many uses, such as in a pharmaceutical composition, a method of treating ZIKV-mediated disease, a method of preventing ZIKV-mediated disease, a method of reducing or preventing the replication of ZIKV in a host cell, a method of controlling the spread of ZIKV in donated tissue, a treated tissue sample, and in the manufacture of a medicament for the treatment or prevention or ZIKV-mediated disease.

20 Claims, 18 Drawing Sheets

Specification includes a Sequence Listing.

(56) References Cited

OTHER PUBLICATIONS

Saleem, M. et al., A conditionally immortalized human podocyte cell line demonstrating nephrin and podocin expression. Journal of the American Society of Nephrology, 2002, p. 630-638, vol. 13, No. 3.

Miner, J. et al., Zika Virus Infection in Mice Causes Panuveitis with Shedding of Virus in Tears, Cell Reports, 2016, p. 3208-3218, vol. 16, No. 12.

PRVABC59 ZIKV Vivo-Morpholino DWK-1 sequence:

5'-CATGACCAGAAACTCTGTTTCCAA-3' morpholino oligonucleotide

Octaguanidine dendrimer

FIG. 5

| | Dose (mg/kg mouse) | Total Alive | Total Dead |
|---|---|---|---|
| Group 1 | 5 | 5 | 0 |
| Group 2 | 10 | 5 | 0 |
| Group 3 | 15 | 5 | 0 |
| Group 4 | 20 | 5 | 0 |
| Group 5 | 30 | 5 | 0 |
| Group 6 | saline | 5 | 0 |

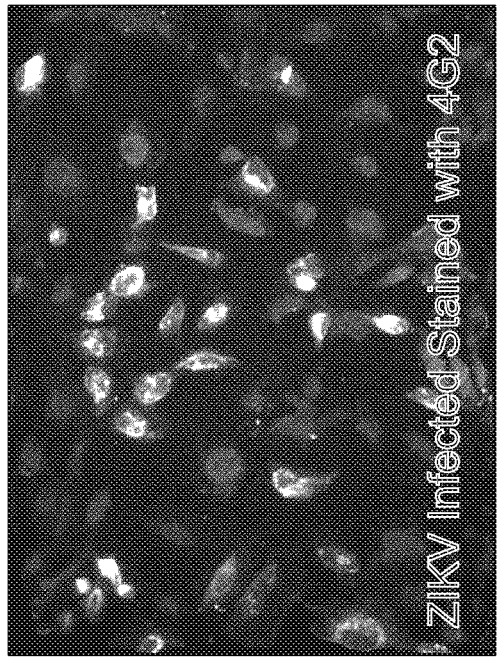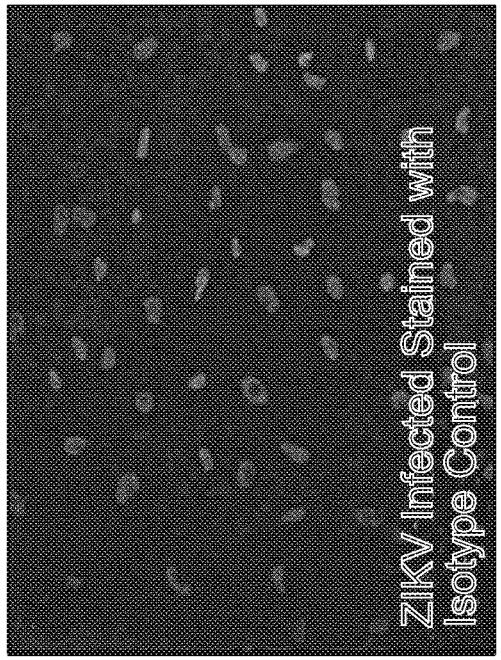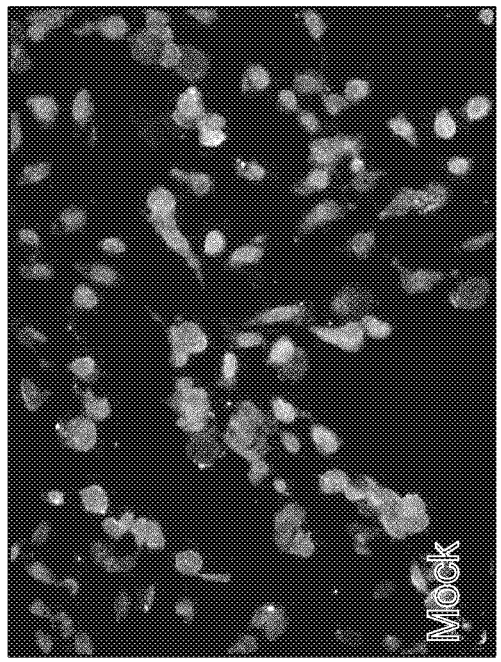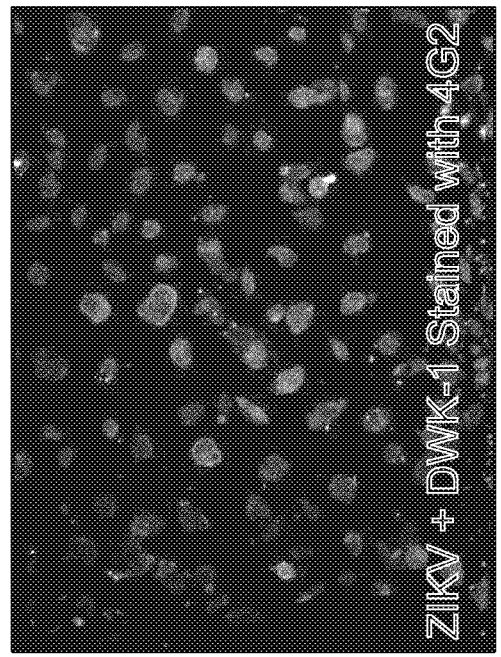

KU955592_ZIKV  CCCCCAAAACGCAAAACAGCATATATTGACGCTGGGAAAGACCAGAGACTCCATGAGTTT
KX377335_ZIKV  CCCCCAAAACGCAAAACAGCATATATTGACGCTGGGAAAGACCAGAGACTCCATGAGTTT

FIG. 13

ANTIVIRAL AGENTS

CROSS-REFERENCE TO RELATED APPLICATIONS

This application is a continuation of, and cites the priority of, PCT/US2017/066270 filed 14 Dec. 2017, which is currently pending, and cites the priority of U.S. Patent Application Nos. 62/434,802 (filed on 15 Dec. 2016) and 62/560,144 (filed on 18 Sep. 2017). All of the foregoing applications are incorporated by reference herein in their entireties.

INCORPORATION-BY-REFERENCE OF SEQUENCE LISTING

The material in the accompanying sequence listing is hereby incorporated by reference in its entirety into this application. The accompanying file, named Sequences_212149_401017.txt, was created on and electronically submitted via EFS-Web on Jun. 28, 2021 and is 45.6 KB.

BACKGROUND

A. Field of the Disclosure

The present disclosure relates generally to medicine, and specifically to antiviral agents. Such agents as well as methods and kits for use therewith are provided.

B. Background

Zika virus (ZIKV) is a member of the Flaviviridae family, genus Flavivirus, which also includes Dengue, West Nile, Japanese encephalitis, and yellow fever viruses. ZIKV is a mosquito-borne arbovirus transmitted primarily by vectors from the Aedes family, in particular Aedes aegypti and Aedes albopictus. ZIKV has quickly spread to more than 50 countries in the Americas and the Caribbean, infecting more than 2 million people. Infection with ZIKV results in asymptomatic disease in 70%-80% of infected individuals; however, ZIKV infection has been strongly associated with increased incidence of Guillain-Barré syndrome and microcephaly in infants. Clinical presentations of ZIKV infection include skin rash, headache, myalgia, joint pain, and conjunctivitis, but is largely self-limiting. However, ZIKV disease in the context of immunosuppression is poorly understood. In a small case study by Nogueira et al., they find that allograft transmission of ZIKV can occur in immunosuppressed SOTp (solid organ transplant patients) resulting in clinical disease in both renal and liver transplant patients. In this study, at admission the four patients infected with ZIKV after transplantation presented with bacterial infection, fever, myalgia, and adynamia along with signs of acute liver or renal damage. They did not have a rash, conjunctivitis, or neurological symptoms, but three of four were anemic and all were thrombocytopenic.

Currently there is no specific treatment or vaccine for ZIKV infection. This represents an urgent unmet medical need for efficacious therapeutics for ZIKV. Even if a vaccine were to be developed, sporadic outbreaks of ZIKV disease could warrant widespread vaccination that may not be cost effective. The need for therapeutic interventions to treat acute disease or timely prophylaxis for immunosuppressed SOTp receiving an allograft from a ZIKV infected donor is essential.

SUMMARY

The problems expounded above, as well as others, are addressed by the invention of an antiviral agent that effectively prevents the replication of ZIKV (although it is to be understood that not all such problems will be addressed by every such embodiment).

In a first aspect, an antiviral agent is provided, comprising a phosphorodiamidate morpholino oligomer comprising an antisense sequence to a portion of a genome of a strain of ZIKV.

In a second aspect, a pharmaceutical composition for the treatment or prevention of a disease mediated by ZIKV is provided, the composition comprising: the antiviral agent above and a pharmaceutically acceptable carrier.

In a third aspect, a method of treatment or prevention of a disease mediated ZIKV in a subject in need thereof is provided, the method comprising administering to the subject a therapeutically effective amount of the pharmaceutical composition above.

In a fourth aspect, a method of reducing or preventing the replication of ZIKV in a host cell is provided, the method comprising contacting the host cell with the antiviral agent above.

In a fifth aspect, a method of controlling the spread of ZIKV in donated tissue is provided, the method comprising exposing the donated tissue to an effective amount of the agent above.

In a sixth aspect, a treated donated tissue sample is provided, comprising a sample of donated tissue and the agent above.

In a seventh aspect, a use of the agent above in the manufacture of a medicament for the treatment or prevention of a disease mediated by ZIKV is provided.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 5: Schematic structure of a Vivo-morpholino. A Vivo-morpholino is composed of a 25-mer long morpholino oligonucleotide covalently linked to an octa-guanidine dendrimer, which serves as a delivery moiety. A nucleotide sequence of ZIKV PRVABC59 Vivo-morpholino DWK-1 (previously referred to as DWK-M1) is shown).

DETAILED DESCRIPTION

A. Definitions

Figure 1A:
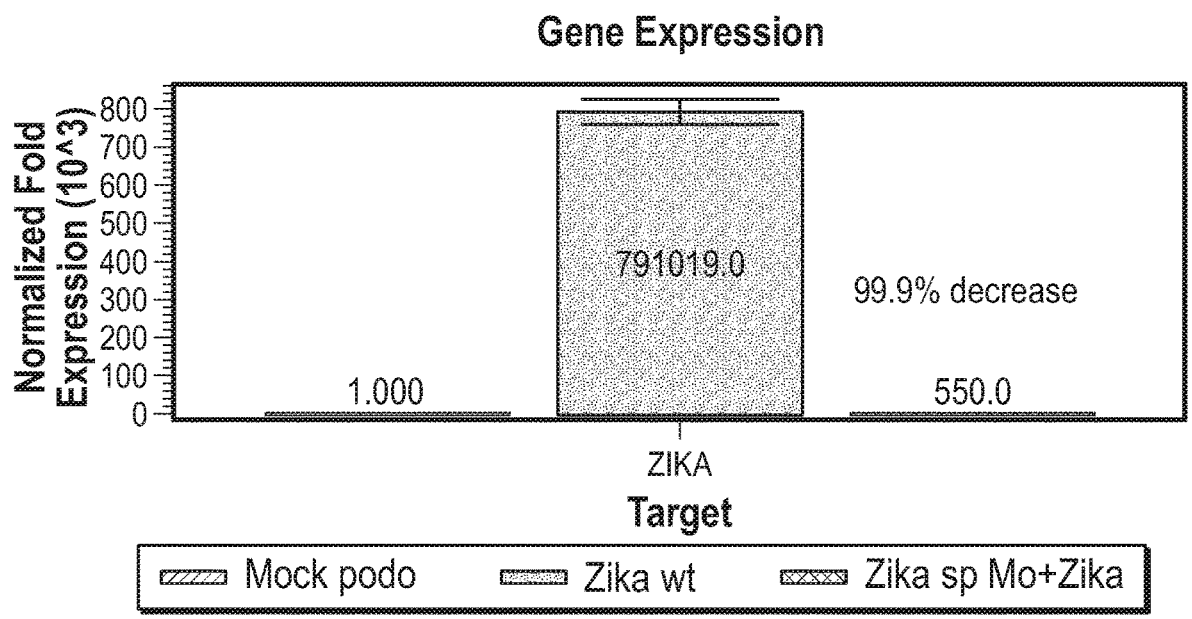
FIGS. 1A and 1B: RT-PCR analysis of human glomerular podocytes infected with ZIKV after treatment with DWK-M1. (1A) Quantitative real-time qRT-PCR analysis of glomerular podocytes infected with ZIKV for 72 h. Shown are mock infected podocytes, podocytes infected with wildtype ZIKV and podocytes pretreated for 24 h with the DWK-M1 morpholino+ZIKV for 72 h. (1B) qRT-PCR analysis of glomerular podocytes infected with ZIKV for 72 h. Shown are mock infected podocytes, podocytes exposed to a control morpholino (Co DWK), podocytes exposed to Co DWK+ZIKV infected, podocytes exposed to DWK-M1 only, podocytes infected with wildtype ZIKV, and podocytes exposed to DWK-M1+ZIKV infected. All values were normalized to GAPDH.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an", and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

Terms such as "administering" or "administration" include acts such as prescribing, dispensing, giving, or taking a substance such that what is prescribed, dispensed, given, or taken actually contacts the patient's body externally or internally (or both). In embodiments of this disclosure, terms such as "administering" or "administration" include self-administering, self-administration, and the like, of a substance. Indeed, it is specifically contemplated that instructions or a prescription by a medical professional to a subject or patient to take or otherwise self-administer a substance is an act of administration.

The terms "prevention", "prevent", "preventing", "suppression", "suppress", and "suppressing", as used herein, refer to a course of action (such as administering a pharmaceutical composition) initiated prior to the onset of a clinical manifestation of a disease state or condition so as to reduce its likelihood or severity. Such reduction in likelihood or severity need not be absolute to be useful.

The terms "treatment", "treat", and "treating", as used herein, refer to a course of action (such as administering a pharmaceutical composition) initiated after the onset of a clinical manifestation of a disease state or condition so as to eliminate or reduce such clinical manifestation of the disease state or condition. Such treating need not be absolute to be useful.

The term "in need of treatment", as used herein, refers to a judgment made by a caregiver that a patient requires or will benefit from treatment. This judgment is made based on a variety of factors that are in the realm of a caregiver's expertise, but that include the knowledge that the patient is ill, or will be ill, as the result of a condition that is treatable by a method or device of the present disclosure.

The term "in need of prevention", as used herein, refers to a judgment made by a caregiver that a patient requires or will benefit from prevention. This judgment is made based on a variety of factors that are in the realm of a caregiver's expertise, but that include the knowledge that the patient will be ill or may become ill, as the result of a condition that is preventable by a method or device of the disclosure.

The terms "individual", "subject", or "patient", as used herein, refer to any animal, including mammals, such as mice, rats, other rodents, rabbits, dogs, cats, swine, cattle, sheep, horses, primates, and humans. The term may specify male or female or both, or exclude male or female.

The term "therapeutically effective amount" (or simply "effective amount"), as used herein, refers to an amount of an agent, either alone or as a part of a pharmaceutical composition, that is capable of having any detectable, positive effect on any symptom, aspect, or characteristics of a disease state or condition. Such effect need not be absolute to be beneficial.

The term "pharmaceutically acceptable salts", as used herein, includes salts of the antiviral agents which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen carbonic, phosphoric, monohydrogen phosphoric, dihydrogen phosphoric, sulfuric, monohydrogen sulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

Nucleic acids are "complementary" to each other, as used herein, when a nucleotide sequence in one strand of a nucleic acid, due to orientation of its nucleotide hydrogen atoms, hydrogen bonds to another sequence on an opposing nucleic acid strand (of course, a strand of a nucleic acid may be self-complementary as well). The complementary bases typically are, in DNA, A with T, and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementarity means that a sequence in one strand is not perfectly complementary to a sequence in an opposing strand, but that sufficient bonding occurs between bases on the two strands to form a stable hybrid complex at a given set of hybridization conditions (e.g., salt concentration and temperature). Such conditions can be predicted by using the sequences and standard models to predict the $T_m$ of hybridized strands, or by empirical determination of $T_m$ by using established methods. $T_m$ refers to the temperature at which a population of hybridization complexes formed between two nucleic acid strands are 50% denatured. At a temperature below the $T_m$, formation of a hybridization complex is favored, whereas at a temperature above the $T_m$, melting or separation of the strands in the hybridization complex is favored. Such stringency is based on the melting temperature ($T_m$) of the nucleic acid binding complex, as taught in Berger and Kimmel (1987, Guide to Molecular Cloning Techniques, Methods in Enzymology, 152, Academic Press, San Diego Calif.). The $T_m$ of an annealed duplex depends on the base composition of the duplex, the frequency of base mismatches, and the ionic strength of the reaction medium. The $T_m$ of a duplex can be calculated by those of ordinary skill in the art based on these two factors using accepted algorithms. Maximum stringency typically occurs at about 5° C. below $T_m$; high stringency at about 5-10° C. below $T_m$; intermediate stringency at about 10-20° C. below $T_m$; and low stringency at about 20-25° C. below $T_m$. As will be understood by those of skill in the art, a maximum stringency hybridization can be used to identify or detect identical nucleotide sequences while an intermediate (or low) stringency hybridization can be used to identify or detect similar or related sequences. Terms such as maximally stringent, highly stringent, and poorly stringent, refer to conditions of maximal stringency, high stringency, and low stringency respectively.

In the following discussion certain outside documents are referenced to enable the reader to make and use the subject matter described herein. Nothing contained herein is to be construed as an "admission" of prior art. Applicant expressly reserves the right to demonstrate, where appropriate, that such documents referenced herein do not constitute prior art under the applicable statutory provisions.

B. Antiviral Agents

A phosphorodiamidate morpholino oligomer (PMO) is disclosed that suppresses viral replication. In the interest of clarity, not all features of an actual implementation are described in this specification. It will of course be appreciated that in the development of any such actual embodiment, numerous implementation-specific decisions must be made to achieve the worker's specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

PMO are nucleic acids having conventional nucleotide bases, but a backbone of methylenemorpholine rings and phosphorodiamidate linkages. PMO bind to RNA with high specificity. This gives PMO the ability to block the translation of mRNA by binding to complementary sequences on the mRNA, which prevents binding of the mRNA to the ribosome. Translational blocking with PMO is highly specific, and does not result in blocking of non-target mRNA. PMO are also much more stable than RNA and resistant to most exonucleases. An unmodified PMO has the following general structure, with each "B" being independently selected from adenine, cytosine, guanine, or thymine:

Form. 1

[Chemical structure diagram]

The PMO of the agent comprises a nucleotide sequence that is complementary to a sequence in a viral genome (the "target sequence"). Such complementary sequence is referred to herein as the "antisense sequence", although as explained below, in some embodiments the sequence may deviate from an exact antisense sequence of the target. The genome may be, without limitation, the genome of a single-stranded positive sense RNA virus, such as a flavivirus. In a specific embodiment of the agent, the genome is a genome of a strain of ZIKV. The sequence in the viral genome should be a sequence that must bind to the cellular ribosome for replication to occur. This may be a sequence in a structural gene (i.e., in an open reading frame), or it may be a non-translated sequence that facilitates binding of the strand to the ribosome.

For purposes of illustration, the ZIKV genome will be used as an example. The ZIKV genome comprises an untranslated 5' region with a methylated cap for canonical cellular translation, a single polyprotein 3419 residues in length, and a non-polyadenylated 3' region that forms stem-and-loop structures. The canonical ZIKV genome is a single-stranded RNA 10,794 base pairs (bp) long. The canonical ZIKV genome has been assigned GENBANK accession number AY632535, and is incorporated herein by reference in its entirety (SEQ ID NO: 1). The ZIKV genome is flanked by 5' untranslated region (UTR) and 3'UTR. The non-coding 3'UTR is highly structured (FIG. 12) with some regions highly conserved between flaviviruses. Without wishing to be bound by any hypothetical model, the interaction between 5' and 3'UTRs are believed to be critical for viral RNA replication. Without wishing to be bound by any hypothetical model, it is believed that RNA elements within the 3'UTR are essential for flavivirus replication and pathogenesis. Among several RNA elements in the 3'UTR, the 3' short hairpin structure (sHP) and 3' stem-loop (3'SL) are highly conserved across flaviviruses and specifically ZIKV strains.

In some embodiments of the agent, the target sequence is a sequence from the 5' region of the ZIKV genome, for example the region encompassing the C (capsid) protein and the 5' untranslated region (UTR). In a specific embodiment of the agent, the target sequence comprises 5'-TTG GAA ACG AGA GTT TCT GGT CAT G-3' (SEQ ID NO: 2) from the 5' UTR. In the same specific embodiment, the PMO comprises the sequence 5'-CAT GAC CAG AAA CTC TCG TTT CCA A-3' (SEQ ID NO: 3). In further embodiments of the agent, the target sequence is a sequence from the 3' region of the ZIKV genome, for example the 3'UTR. Again turning to FIG. 12, the 3'UTR of the ZIKV genome contains three stem-and-loop structures (SL I, SL II, and SL III), a 3' short hairpin structure (sHP), and a terminal 3' end stem-and-loop structure. Various embodiments of the antiviral agent target one or more of these 3' structures. The sHP is particularly highly conserved among strains of ZIKV (FIG. 13) (SEQ ID NOS: 26 and 27 for KU955592_ZIKV and KX377335_ZIKV, respectively). A specific embodiment of the antiviral agent targets a sequence in the sHP. In a specific embodiment of the agent, the target sequence comprises 5'-GCT GGG AAA GAC CAG AGA CTC CAT G-3' (SEQ ID NO: 4) from the sHP. In the same specific embodiment, the PMO comprises the sequence 5'-CAT GGA GTC TCT GGT CTT TCC CAG C-3 (SEQ ID NO: 5).

The antisense sequence will bind with high stringency to the target sequence under physiological (intracellular) conditions. Such conditions are understood by those of ordinary skill in the art, but will vary by cell type. For example, intracellular pH and sodium concentration varies in a narrow range by cell type. Physiological conditions for human subjects are generally at 37° C. (98.6° F.). Typically, this means that the antisense sequence will have at least 80% identity with an exact complement of the target sequence. In various embodiments of the agent the antisense sequence will have at least 85, 90, 95%, 96%, 97%, 98%, or 99% identity with an exact complement of the target sequence. In a specific embodiment the antisense sequence is an exact complement of the target sequence.

The antisense sequence will generally be about 25 bases long. This can vary somewhat, in the range of about 10-30 bases. Specific embodiments of the antisense sequence can be any length from 10-30 bases. More specific embodiments are 15-25 bases. A particular embodiment of antisense sequence is exactly 25 bases long. The PMO may comprise additional nucleotides on the 5' end or 3' end (or both) of the target recognition sequence. In a specific embodiment, the antisense sequence is the entire nucleotide sequence of the PMO, and there are no additional nucleotides on the 5' end or the 3' end of the antisense sequence.

The PMO may have other various desirable characteristics. These may include without limitation: a base sequence that has very little self-complementarity; a high enough GC-content (guanine-cytosine content) (e.g. 40-60%) so that it has a high target affinity; and no stretches of four or more contiguous G to preserve water solubility.

The PMO may have modified 3' or 5' ends to add various additional functionalities. Such modifications can include 3' conjugation with any of: a fluorophore, a quencher, carboxyfluorescein, lissamine, dabcyl, biotin, amine, amine with biotin, disulfide amine, pyridyl dithio, azide, and alkyne. Such modifications may include 5' conjugation with any of: a primary amine, dabcyl, azide, and alkyne. In a specific embodiment of the agent, the PMO is modified for intracellular delivery.

Modifications for cellular delivery may include endocytosis-stimulating peptides, such as weak-base amphiphilic peptides taught in U.S. Pat. No. 7,084,248 and commercially available under the tradename ENDO PORTER from Gene Tools, LLC (Philomath, Oreg., USA). In another example, the PMO is conjugated to an octa-guanidine dendrimer. A specific embodiment of the octa-guanidine dendrimer has the following structure:

Form. 2

C. Pharmaceutical Compositions

A pharmaceutical composition for treating or preventing a disease mediated by ZIKV is provided, the composition comprising any of the antiviral agents provided above. The compositions disclosed may comprise one or more of such antiviral agents, in combination with a pharmaceutically acceptable carrier. Examples of such carriers and methods of formulation may be found in Remington: The Science and Practice of Pharmacy (20th Ed., Lippincott, Williams & Wilkins, Daniel Limmer, editor), and are generally well understood by those skilled in the art. To form a pharmaceutically acceptable composition suitable for administration, such compositions will contain a therapeutically effective amount of an antiviral agent.

The pharmaceutical compositions of the disclosure may be used in the treatment and prevention methods of the present disclosure. Such compositions are administered to a subject in amounts sufficient to deliver a therapeutically effective amount of the antiviral agent so as to be effective in the treatment and prevention methods disclosed herein. The therapeutically effective amount may vary according to a variety of factors such as the subject's condition, weight, sex, and age. For example, some embodiments of the composition comprise up to the median lethal dose ($LD_{50}$) of the antiviral agent. The $LD_{50}$ can be ascertained using standard toxicological methods, or by reference to past studies. Alternatively, the pharmaceutical composition may be formulated to achieve a desired concentration of the antiviral agent at the site of the infection.

The toxicity of PMO are generally very low. Embodiments of the antiviral agent have been tested for toxicity in mice (see Example 4 below). No mortality was observed at up to 30 mg/kg. In some embodiments of the pharmaceutical composition, the PMO is administered to the subject at up to about 30 mg/kg. In further embodiments of the pharmaceutical composition, the PMO is administered to the subject at up to about 5, 10, 15, or 20 mg/kg. To account for possible interspecies variation in sensitivity to the agent, in further embodiments of the pharmaceutical composition, the PMO is administered to the subject at up to about 0.5, 1, 1.5, 2, or 3 mg/kg. To further account for possible variation among individuals and interspecies variation, in further embodiments of the pharmaceutical composition, the PMO is administered to the subject at up to about 0.05, 0.1, 0.15, 0.2, or 0.3 mg/kg. The PMO may be administered to the subject, such as in a pharmaceutical composition, to provide the PMO at a dosage/body mass concentration of up to an amount selected from: 0.05, 0.1, 0.15, 0.2, 0.3, 0.5, 1, 1.5, 2, 3, 5, 10, 15, 20, 30 mg/kg, about any of the foregoing values, and a range between any of the foregoing values.

Other factors include the mode and site of administration. The pharmaceutical compositions may be formulated to be provided to the subject in any method known in the art. Exemplary dosage forms include ocular, subcutaneous, intravenous, topical, epicutaneous, oral, intraosseous, intramuscular, intranasal, and pulmonary. The compositions of the present disclosure may be formulated to be administered only once to the subject or more than once to the subject. Furthermore, when the compositions are administered to the subject more than once, they may be formulated for a variety of regimen, such as once per day, once per week, once per month, or once per year. The compositions may also be formulated to be administered to the subject more than one time per day. The therapeutically effective amount of the antiviral agent and appropriate dosing regimens may be identified by testing in order to obtain optimal activity, while minimizing any potential side effects. In addition, formulation for co-administration or sequential administration of other agents may be desirable.

The compositions of the present disclosure may be formulated to be administered systemically, such as by intravenous administration, or locally such as by subcutaneous injection or by application of a gel, fiber, paste, or cream.

The compositions of the present disclosure may further comprise agents which improve the solubility, half-life, absorption, etc. of the antiviral agent. Furthermore, the compositions of the present disclosure may further comprise agents that attenuate undesirable side effects and/or decrease the toxicity of the antiviral agent. Examples of such agents are described in a variety of texts, such as Remington: The Science and Practice of Pharmacy (20th Ed., Lippincott, Williams & Wilkins, Daniel Limmer, editor).

The compositions of the present disclosure can be formulated in a wide variety of dosage forms for administration. For example, the compositions can be in the form of tablets, capsules, sachets, lozenges, troches, pills, powders, granules, elixirs, tinctures, solutions, suspensions, syrups, ointments, creams, pastes, emulsions, or solutions for intravenous administration or injection. Other dosage forms include for administration transdermally, via patch mechanism or ointment. Further dosage forms include formulations suitable for delivery by nebulizers or metered dose inhalers. Any of the foregoing may be modified to provide for timed release and/or sustained release formulations.

In the present disclosure, the pharmaceutical compositions may further comprise a pharmaceutically acceptable carrier. Such carriers may include vehicles, adjuvants, surfactants, suspending agents, emulsifying agents, inert fillers, diluents, excipients, wetting agents, binders, lubricants, buffering agents, disintegrating agents, accessory agents, coloring agents, and flavoring agents (collectively referred to herein as a carrier). Typically, the pharmaceutically acceptable carrier is chemically inert to the antiviral agents and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, in compositions for oral administration in solid form, such as tablets, capsules, sachets, lozenges, troches, pills, powders, or granules, the antiviral agent may be combined with an oral, non-toxic pharmaceutically acceptable inert carrier, such as inert fillers, suitable binders, lubricants, disintegrating agents, and accessory agents. Suitable binders include, without limitation, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthan gum, and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The composition may be also be in oral liquid form, such as a tincture, solution, suspension, elixir, and syrup; and the antiviral agents of the present disclosure can be dissolved in diluents, such as water, saline, or alcohols. Furthermore, the oral liquid forms may comprise suitably flavored suspending or dispersing agents such as synthetic and natural gums, for example, tragacanth, acacia, methylcellulose, and the like. Moreover, when desired or necessary, suitable coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The composition may comprise a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap, an oil or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include: (a) cationic detergents such as, for example, dimethyldialkylammonium halides, and alkylpyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylene polypropylene copolymers; (d) amphoteric detergents such as, for example, alkylbeta-aminopropionates, and 2-alkylimidazoline quaternary ammonium salts; and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as ointments, creams, pastes, and emulsions, containing the antiviral agent, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage, or dressing for transdermal delivery, or may be applied to a bandage or dressing for delivery directly to the site of a wound or cutaneous injury.

The antiviral agents of the present disclosure can also be formulated to be administered in the form of liposome delivery systems, such as small unilamellar vesicles, large unilamellar vesicles and antiemetics. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The antiviral agents of the present disclosure may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the antiviral agents of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates, and cross-linked or amphipathic block copolymers of hydrogels.

D. Methods of Use

By way of non-limiting example only, methods of using the agents and pharmaceutical compositions disclosed above are provided.

A method of treatment or prevention of a disease mediated by ZIKV in a subject in need thereof is provided, the method comprising administering to the subject a therapeutically effective amount of any of the pharmaceutical compositions disclosed above. The disease may be any that is caused, complicated, or exacerbated by ZIKV infection, including Zika fever, Guillain-Barré syndrome, a congenital defect, microcephaly, ocular disease, and Zika associated organ pathology. The ZIKV infection need not be in the subject him or herself; for example, the method could be used for the prevention of microcephaly in a fetus by administration to the mother.

The method of treatment and/or prevention comprises administering to the subject the antiviral agent in an amount sufficient to treat or prevent the ZIKV-mediated disease (therapeutically effective amount). The method will often further comprise identifying a subject in need of such treatment or prevention. Too little antiviral agent would fail to provide the therapeutic effect. On the other hand, excessive antiviral agent could lead to undesired side effects.

The therapeutically effective amount may vary according to a variety of factors such as the subject's condition, weight, sex and age. For example, some embodiments of the method comprise administration of up to the median lethal dose ($LD_{50}$) of the antiviral agent. The $LD_{50}$ can be ascertained using standard toxicological methods, or by reference to past studies. Alternatively, the method may comprise delivering a desired concentration of the antiviral agent to a tissue, organ, or cell type hosts ZIKV in the subject.

If, after the administration of the antiviral agent, the subject still has the ZIKV-mediated disease, or is at risk for the same, then an optional step of the method is to continue administration of the antiviral agent or pharmaceutical composition.

In one embodiment, the method comprises delivering the antiviral agent to a tissue, organ, or cell type of the subject that hosts ZIKV. Such tissues and organs include the eye, retinal tissue, retinal endothelial cells, retinal microvascular endothelial cells, retinal pigmented epithelial cells, retinal pericytes, kidney, glomerular tissue, glomerular podocytes, renal glomerular endothelial cells, mesangial cells, cytotrophoblasts, syncytiotrophoblast, human brain microvascular endothelial cells, human neural stem cells, astrocytes, neuroblastoma cells, neural progenitor cells, placental endothelial cells, placental fibroblasts, Hofbauer cells, amniotic epithelial cells, chorionic villi cells, keratinocytes, dermal fibroblasts, dendritic cells, umbilical vein endothelial cells, aortic endothelial cells, coronary artery endothelial cells, saphenous vein endothelial cells, glial cells, primary spermatocytes, Sertoli cells, retinal bipolar cells, retinal ganglion cells, optic nerve cells, and Vero cells. It is desirable to deliver the antiviral agent to such targets because they are the sites of infection and replication. Targeted delivery could also prevent unwanted effects on other tissues or organs. In an alternate embodiment, the method comprises administering the antiviral agent locally to the subject's eye.

A method of reducing or preventing the replication of ZIKV in a host cell is provided, the method comprising contacting the host cell with an effective concentration any of the antiviral agents described above. In a specific embodiment of the method the effective concentration is at least about 10, 12, 15, or 20 µM. In a further specific embodiment of the method the effective concentration is about 10, 12, 15, or 20 µM, or any subrange thereof. The host cell may be situated in vivo or ex vivo, and may be any cell type known to be permissive to ZIKV, including any of those listed above.

A method of controlling the spread of ZIKV in donated tissue is provided, the method comprising exposing the donated tissue to an effective amount of any embodiment of the antiviral agent disclosed above. The donated tissue may be in the form of a donated organ. The organ or tissue may be exposed to the antiviral agent by perfusing the organ or tissue with a solution containing the effective concentration of the antiviral agent. In a specific embodiment of the method the effective concentration is at least about 10, 12, 15, or 20 µM. In a further specific embodiment of the method the effective concentration is about 10, 12, 15, or 20 µM, or any subrange thereof. The antiviral agent may be part of an organ preservation composition, such as University of Wisconsin cold storage solution (available from Bridge to Life Ltd., Columbia, S.C.) or any other organ preservation solution known in the art. Another aspect of the disclosed work is a treated donated organ or tissue, comprising an organ preservation composition that includes an effective amount of any of the antiviral agents listed above.

E. Working Example 1

The use of PMO based technology targeting the nucleotide translation initiation complex site of ZIKV for antiviral development was explored.

Human glomerular podocytes were obtained from Dr. Moin A. Saleem [14] and were cultured as described in [15]. All cells were trypsinized and plated on uncoated 4.2 cm$^2$/well glass chamber slides at density 2.5×10$^5$ cells per well or in 6 well dishes at a concentration 3.5×10$^5$ per well.

A lyophilized, modified PMO was dissolved in sterile water to a final concentration of 0.5 mM. The PMO was a 25-mer having the sequence 5'-CAT GAC CAG AAA CTC TCG TTT CCA A-3' (SEQ ID NO: 4). The PMO was modified by the addition of an octa-guanidine dendrimer of the following structure:

Form. 2

This modified PMO was dubbed DWK-M1.

A 30 µL aliquot was added to podocytes cultured in fresh 1.5 mL RPMI media supplemented with 2% FCS and insulin-transferrin-selenium (ITS) per well of 6-well dishes. The final concentration of the modified PMO culture medium was 10 µM. After 24 hours of incubation, podocytes were rinsed with RPMI supplemented with 10% FCS and ITS and either mock infected or infected with ZIKV and cultured for the indicated time.

The ZIKV strain PRVABC59 was used, originally isolated from a human serum specimen from Puerto Rico in December 2015, nucleotide (GenBank): KU501215 ZIKV strain PRVABC59 [1-3]. The virus was cultivated in Vero cells (*Cercopithecus aethiops*, kidney cell line) and infectious supernatant was filtered using a 0.22 μm filter and the serum content adjusted to 15%. Stock viral titers were done by florescent focus assays (FFA) on Vero cells using the 4G-2 Flavivirus group antigen monoclonal antibodies from Millipore (Temecula, Calif., USA) ("4G-2 antibody") and was adjusted to about $1\times10^4$ particles/5 μL of infectious culture supernatant.

Total RNA was extracted from ZIKV infected podocytes, along with the respective mock infected cells, or podocytes pretreated with control or the modified PMOs and infected with ZIKV using a Qiagen RNeasy Mini Kit (Qiagen, Valencia, Calif., USA). Messenger RNA in 0.5 μg of each sample was primed using random hexamers and reverse transcribed with a high capacity cDNA reverse transcription kit (Applied Biosystems, Foster City, Calif., USA). Real-time quantitative PCR was performed on iCycler96 using iQ Sybr Green Supermix (Bio-Rad). Samples were analyzed in triplicate and normalized to GAPDH RNA. Reaction mixture contained 250 nM of each primer and 200 to 400 ng of template cDNA in a final volume of 20 μL. The primers specific for ZIKV were as follows: forward 5' AGG ATC ATA GGT GAT GAA GAA AAG T 3' (SEQ ID NO: 6) and reverse 5' CCT GAC AAC ACT AAG ATT GGT GC 3' (SEQ ID NO: 7) [4]. GAPDH primers used for qRT-PCR were as follows: forward: 5'-GAA GGT GAA GGT CGG AGT-3' (SEQ ID NO: 8) and reverse: 5'-GAA GAT GGT GAT GGG ATT TC-3' (SEQ ID NO: 9).

Immunofluorescent staining was performed. Briefly, chamber slide cultures containing mock infected human podocytes, podocytes infected with ZIKV and podocytes infected ZIKV after 24 hours pre-treatment with the modified PMO. Cells were washed twice with PBS pH 7.4, air dried, and fixed in absolute methanol for 20 min at −20° C. Cells were air dried for 10 min, hydrated in Tris buffered saline (pH 7.6) for 10 min, and incubated for 1 h with 4G-2 antibody at a dilution 1:100 in PBS pH 7.4 [5].

For the western blot analysis, cell extracts were prepared using RIPA lysis buffer (50 mM Tris pH 7.5, 150 mM NaCl, 2 mM ethylenediaminetetraacetic acid (EDTA) pH 8.0, 1% NP40, 0.5% sodium deoxycholate, 0.1% sodium dodecyl sulfate (SDS), and proteinase inhibitor (Complete Ultra, Roche)). Lysates were incubated on ice for 30 minutes and then clarified by centrifugation. Total protein was measured by micro BCA protein assay kit (ThermoFisher Scientific). 30 μg of protein lysates from paired, mock and ZIKV and PMO controls with and without ZIKV infection were separated by 10% SDS-PAGE gels, transferred to nitrocellulose membranes (Bio-Rad), blocked with 5% milk in 0.1% TBST (0.1% Tween 20, 20 mM Tris, 150 mM NaCl) and incubated at 4° C. overnight with 4G-2 antibody at 1:250 dilution. Synaptopodin antibody (Santa Cruz Biotechnology) was used at 1:250 dilution and GAPDH antibody (Santa Cruz Biotechnology) at 1:3000 dilution. Membranes were washed five times in 0.1% TBST and incubated for one hour with corresponding secondary antibody conjugated with HRP (ThermoFisher Scientific) at a dilution of 1:50,000. Immunoreactive bands were detected with WesternBright ECL (Advansta) following exposure to X-ray film.

Experiments presented in this example were performed in triplicate. To compare the mean values between two groups, the unpaired t-test was used. Statistical significance was defined as $P<0.05$. Data are presented as means±SD. qRT-PCR experiments were replicated three times and normalized to glyceraldehyde 3-phosphate dehydrogenase (GAPDH).

Advantageously, the modified PMO was found to inhibit ZIKV transcription in infected human glomerular podocytes. Without being bound by any particularly theory, it is believed that ZIKV enters a permissive cell via receptor mediated endocytosis. Acidification of the endosome results in breakdown of the viral nucleocapsid and release of the positive, sense genomic RNA. The modified PMO efficiently binds to ZIKV genomic RNA to block translation of the ZIKV polyprotein precursor. The modified PMO was found to inhibit ZIKV transcription in infected human glomerular podocytes that are highly permissive for ZIKV infection. As qRT-PCR showed, podocytes pretreated for 24 hours prior to ZIKV infection with 10 μM of the modified PMO can reduce ZIKV RNA expression by 1438-fold (99.9% reduction) after 72 hours as compared to mock and ZIKV infected controls (FIG. 1A).

Figure 1B:
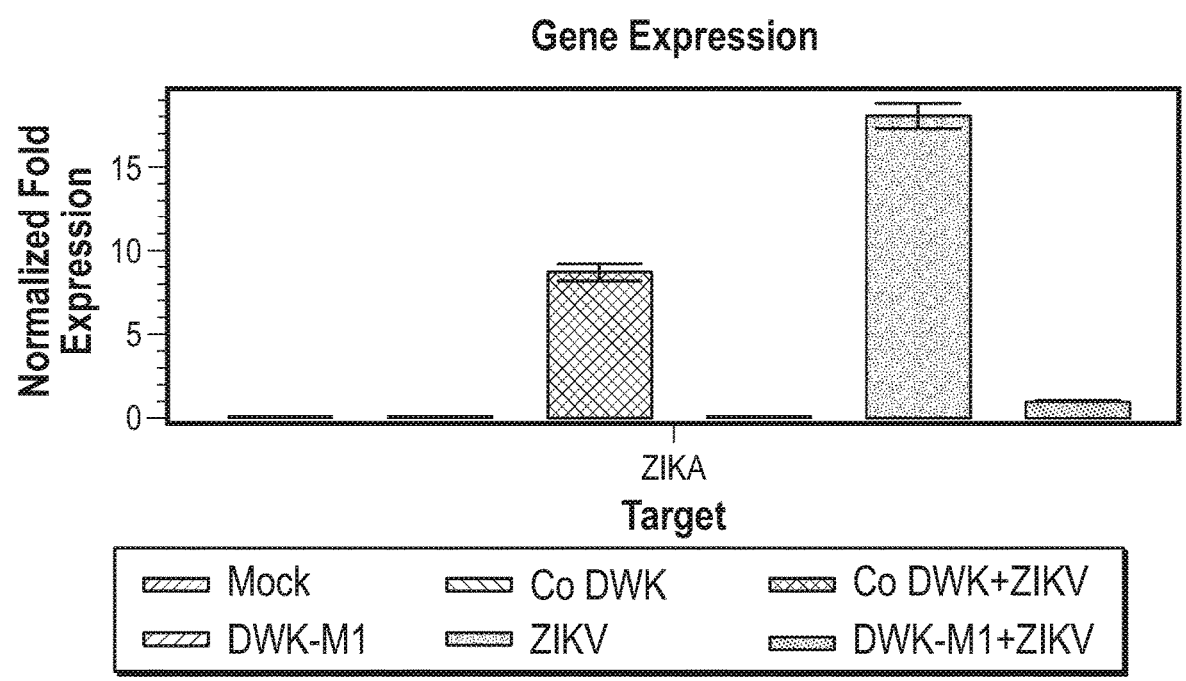

The test was repeated to include mock infected podocytes, podocytes exposed to a control PMO, podocytes exposed to the control PMO+ZIKV infected, podocytes exposed to the modified PMO alone, podocytes infected with wildtype ZIKV, and podocytes exposed to the modified PMO+ZIKV infected (FIG. 1B). Results showed that mock infected podocytes, podocytes exposed to the control PMO or the modified PMO alone showed no detectable (ND) levels of ZIKV RNA expression after amplification (FIG. 1B). Podocytes exposed the control PMO and infected with ZIKV showed increased levels ZIKV RNA compared to mock infected controls. Podocytes exposed to wildtype ZIKV showed increased levels of ZIKV RNA expression but podocytes exposed to the modified PMO and infected with wildtype ZIKV showed 94% decrease in ZIKV RNA expression compared to podocytes infected with wildtype ZIKV (FIG. 1B).

Figure 2:
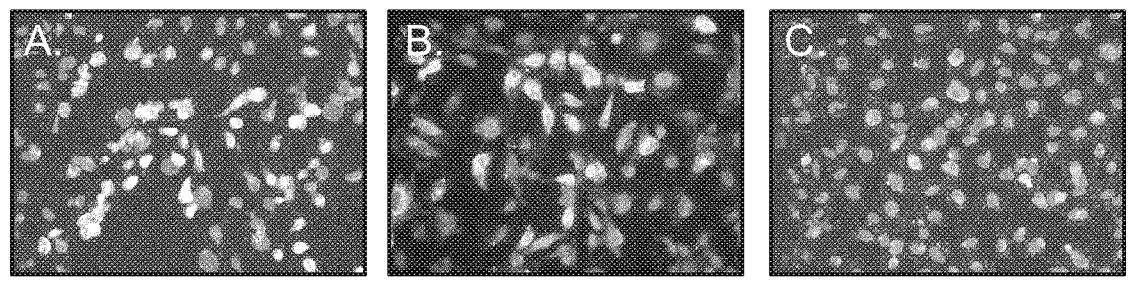
FIG. 2: Immunofluorescent staining of ZIKV infected podocytes using the 4G-2 antibody to the E-protein of ZIKV, (A) mock infected podocytes stained with 4G-2 antibody (B) podocytes infected with wildtype ZIKV for 72 h and stained with the 4G-2 antibody (C) podocytes pretreated with DWK-M1 for 24 h then infected with ZIKV for 72 h and stained with the 4G-2 antibody. Phase and fluorescent images were taken on a Nikon TE2000S microscope mounted with a charge-coupled device (CCD) camera at 200× magnification. For fluorescent images, 4',6-diamidino-2-phenylindole (DAPI) was used to stain the nuclei blue.
Figure 3:
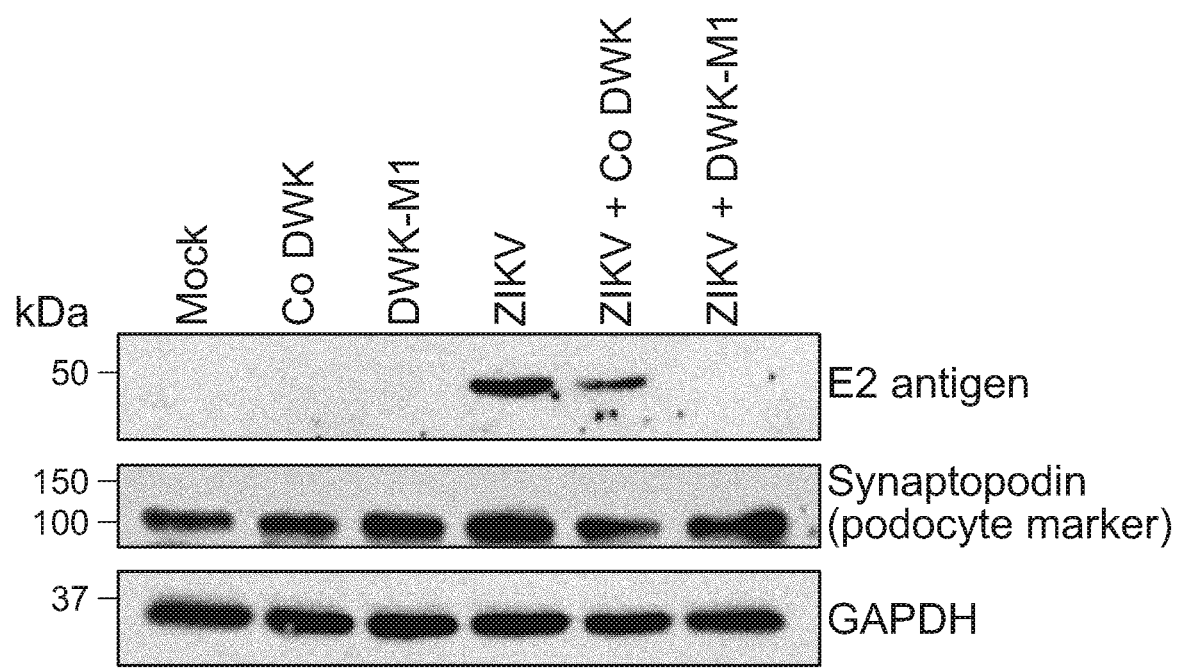
FIG. 3: Shown is a western blot analysis of protein lysates from ZIKV infected podocytes. Results include mock infected podocytes, podocytes exposed to a control morpholino (Co DWK), podocytes exposed to the Co DWK and ZIKV infected, podocytes exposed to DWK-M1 alone, podocytes infected with wildtype ZIKV, and podocytes exposed to DWK-M1+ZIKV infected. The ZIKV expression of the E protein (E2 antigen) is shown in the top panel. The middle panel shows the podocyte marker Synaptopodin and bottom panel shows GAPDH as a loading control.

The modified PMO was found to inhibit ZIKV replication and protein synthesis in podocytes to undetectable levels. To determine if the modified PMO inhibition ZIKV transcription in infected human glomerular podocytes would result in a decrease in ZIKV protein expression, ZIKV total protein expression after the modified PMO treatment of infected podocytes by immunofluorescent staining and immunoblot analysis was examined (FIGS. 2 and 3). The 4G-2 antibody did not stain mock infected podocytes, while podocytes infected with wildtype ZIKV for 72 hours showed characteristic perinuclear staining with the 4G-2 antibody (FIG. 2). Podocytes pre-treated with the modified PMO and infected with wildtype ZIKV for 72 hours showed no specific expression of ZIKV proteins after infection as shown by negative staining with the 4G-2 antibody and by comparison to mock infected cells (FIG. 2). In addition, ZIKV total E-protein expression after treatment with the modified PMO for 72 hours was subjected to immunoblot analysis (FIG. 3). In the immunoblot analysis, it was observed that ZIKV E-protein expression in both podocytes infected with wildtype ZIKV and podocytes exposed to the PMO control (Co DWK)+ ZIKV. Higher levels of ZIKV E-protein was observed in podocytes infected with wildtype ZIKV compared to podocytes exposed to the PMO control (Co DWK)+ZIKV (FIG. 3). However, podocytes pretreated with the modified PMO and infected with wildtype ZIKV showed no detectable levels of ZIKV E-protein (FIG. 3). Moreover, the expression of the podocyte marker Synaptopodin was not effected by ZIKV infection or podocyte exposure to the control PMO or the modified PMO (FIG. 3).

Figure 4A:
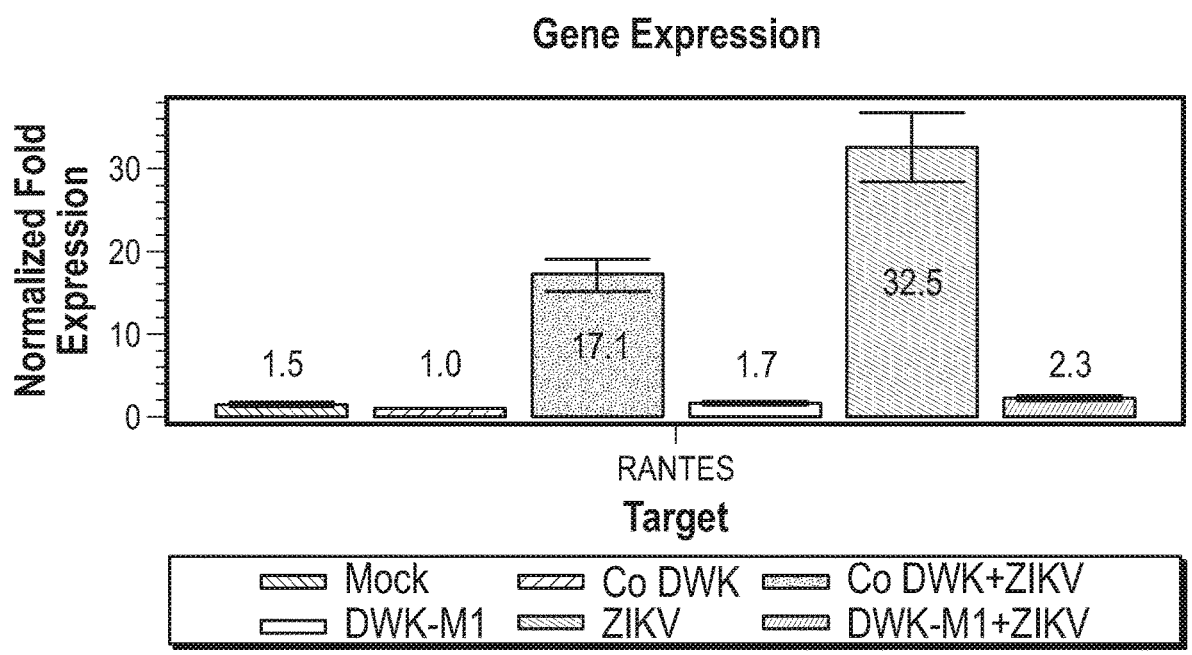
FIG. 4A: Real time PCR analysis of podocytes infected with ZIKV after exposure to DWK-M1 72 hours after infection for RANTES. Results show ZIKV induction of RANTES in podocytes after 24 h pretreatment with the Co DWK, and the DWK-M1 morpholinos. Mock infected and morpholino controls without ZIKV are also shown. All values were normalized to GAPDH.
Figure 4B:
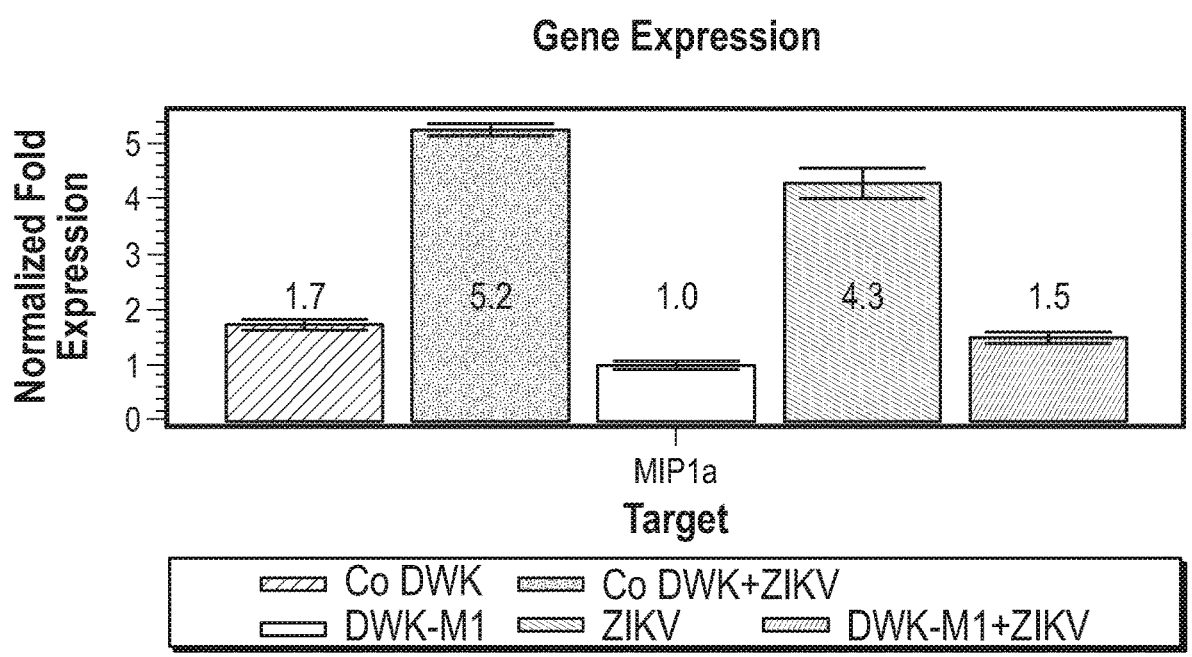
FIG. 4B: Real time PCR analysis of podocytes infected with ZIKV after exposure to DWK-M1 72 hours after infection for MP1-alpha. Results show ZIKV induction of MIP-1alpha in podocytes after 24 h pretreatment with the Co DWK, and the DWK-M1 morpholinos. Mock infected and morpholino controls without ZIKV are also shown. All values were normalized to GAPDH.
Figure 4C:
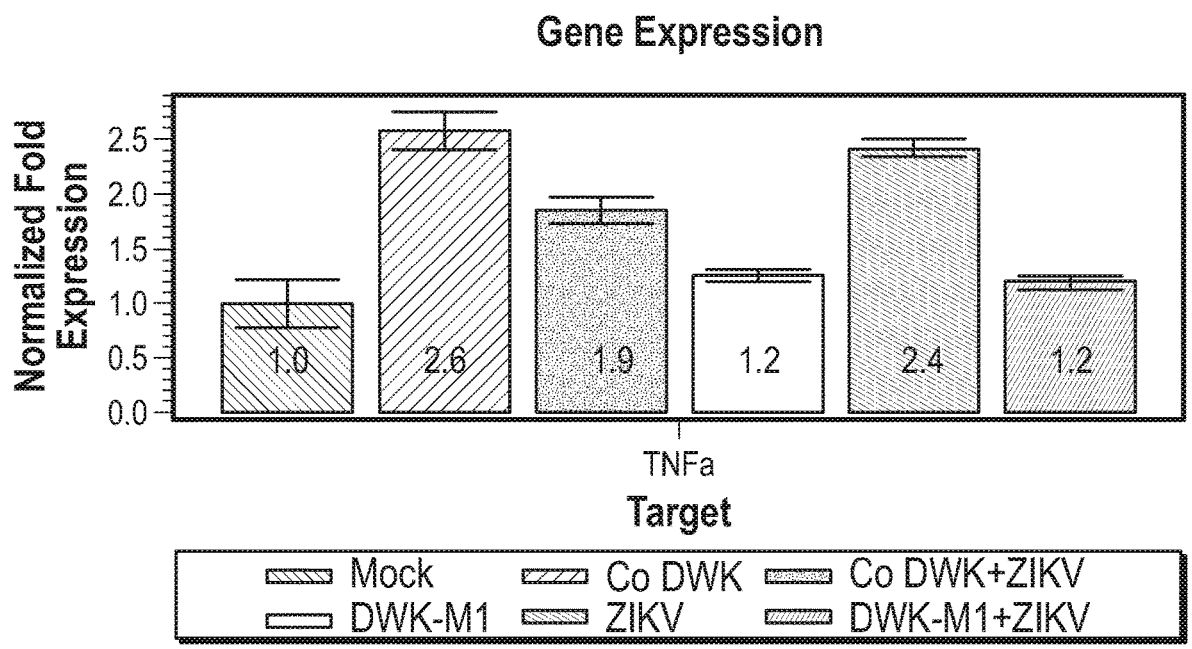
FIG. 4C: Real time PCR analysis of podocytes infected with ZIKV after exposure to DWK-M1 72 hours after infection for TNFα. Results show ZIKV induction of TNF-alpha in podocytes after 24 h pretreatment with the Co DWK, and the DWK-M1 morpholinos. Mock infected and morpholino controls without ZIKV are also shown. All values were normalized to GAPDH.
Figure 4D:
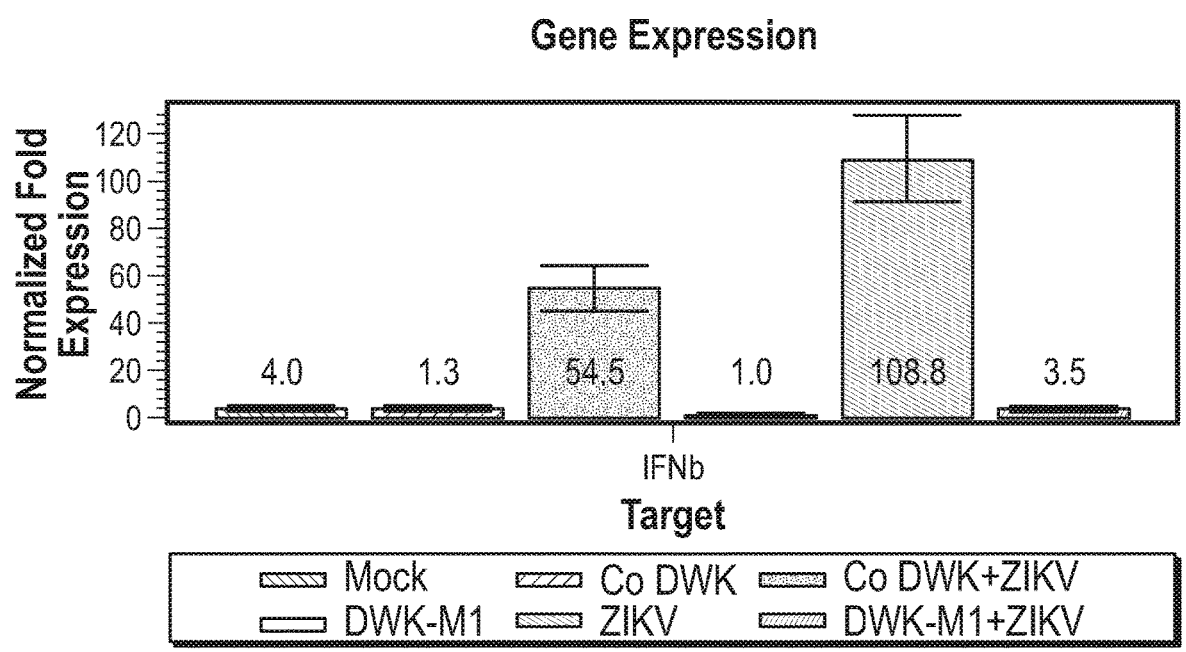
FIG. 4D: Real time PCR analysis of podocytes infected with ZIKV after exposure to DWK-M1 72 hours after infection for IFN-b. Results show ZIKV induction of INF-b in podocytes after 24 h pretreatment with the Co DWK, and the DWK-M1 morpholinos. Mock infected and morpholino controls without ZIKV are also shown. All values were normalized to GAPDH.

The modified PMO was found to inhibit ZIKV induced inflammation in podocytes. Mock infected podocytes, podocytes exposed to the control PMO, podocytes exposed to the control PMO+ZIKV, podocytes exposed to the modified PMO alone, podocytes infected with wildtype ZIKV, and podocytes exposed to the modified PMO+ZIKV by qRT-PCR for ZIKV induction of RANTES, MIP-1alpha, TNF-alpha, and INF-b were examined (FIGS. 4A-4D). Results showed increased levels of RANTES (FIG. 4A), MIP-1 alpha (FIG. 4B), TNF alpha (FIG. 4C) and INF-b (FIG. 4D) in ZIKV infected podocytes compared to control cells that were not exposed to ZIKV (FIGS. 4A-4D). An upregulation of RANTES expression was observed 72 hours after ZIKV infection in both podocytes exposed to the control PMO+ZIKV and in podocytes infected with wildtype ZIKV (FIG. 4A). However, a suppression of RANTES transcription was observed in podocytes pretreated with the modified PMO prior to ZIKV infection as compared to levels detected in podocytes exposed to wildtype ZIKV (FIG. 4A). However, no induction of RANTES expression was detected in mock podocytes or podocytes exposed to the modified PMO alone (FIG. 4A). Lower levels of RANTES transcription were observed in podocytes exposed to the control PMO+ZIKV compared to podocytes infected with wildtype ZIKV only (FIG. 4A). Upregulation was detected of MIP-1 alpha, TNF-alpha and IFN-b mRNA expression 72 hours after ZIKV infection in both podocytes exposed to the control PMO+ZIKV and in podocytes infected with wildtype ZIKV (FIGS. 4B, 4C, and 4D). There was suppression of MIP-1 alpha, TNF-alpha, and IFN-b transcription in podocytes exposed to the modified PMO prior to ZIKV infection compared to podocytes exposed to wildtype ZIKV (FIGS. 4B, 4C, and 4D). However, no significant induction of MIP-1 alpha, TNF-alpha, and IFN-b expression was detected in mock podocytes or podocytes exposed to the modified PMO alone (FIGS. 4B, 4C, and 4D). Lower levels were observed of MIP-1 alpha, TNF-alpha, and IFN-b transcription in podocytes exposed to the control PMO+ZIKV compared to podocytes infected with wildtype ZIKV only (FIGS. 4B, 4C, and 4D).

In this example, the effectiveness of the ZIKV specific PMO ("the modified morpholino" or "DWK-M1") was surprisingly found to suppress active transcription of ZIKV in vitro by 1438-fold, or 99.9%. The modified PMO was shown to reduce ZIKV total E-protein expression to undetectable levels. In addition, it was shown that the modified PMO has no effect on the steady state expression levels of the podocyte specific biomarker synaptopodin. Furthermore, it was shown that the modified PMO suppresses ZIKV induced RANTES, MIP-1 alpha, TNF-alpha, and INF-b to levels observed in mock infected control cells.

REFERENCES

1. Lanciotti R S, Lambert A J, Holodniyet M, et al. 2016. Phylogeny of Zika Virus in Western Hemisphere, 2015. Emerg Infect Dis 2016; 5: 933-35.
2. Thomas D L, Sharp T M, Torres J, et al. Local Transmission of Zika Virus—Puerto Rico, Nov. 23, 2015-Jan. 28, 2016. MMWR Morb Mortal Wkly Rep 2016; 6:154-58.
3. Dirlikov E, Ryff K R, Torres-Aponte J, et al. 2016. Update: Ongoing Zika Virus Transmission—Puerto Rico, Nov. 1, 2015-Apr. 14, 2016. MMWR Morb Mortal Wkly Rep 2016; 17:451-55.
4. Xu M Y, Liu S Q, Deng C L, et al. Detection of Zika virus by SYBR green one-step real-time RT-PCR. J Virol Methods 2016; 236:93-7.
5. Wilkerson I, Laban J, Mitchell J M, et al. Retinal pericytes and cytomegalovirus infectivity: implications for HCMV-induced retinopathy and congenital ocular disease. J Neuroinflammation 2015; 12: 2.

F. Working Example 2

In Working Example 2, the use of a morpholino oligonucleotide targeted to the 5' untranslated region (5'-UTR) of the ZIKV RNA to prevent ZIKV replication was explored. Vivo-morpholino oligonucleotide DWK-1 was used at 10 μM concentration, and inhibition of ZIKV replication in human glomerular podocytes treated with DWK-1 was analyzed by qRT-PCR, reduction in ZIKV genome copy number, western blot analysis, immunofluorescence and proinflammatory cytokine gene expression in ZIKV infected podocytes pretreated with DWK-1. An approximately 95% reduction in ZIKV transcription in podocytes pretreated with DWK-1 followed by 72 h exposure to ZIKV when compared to controls was shown. Immunofluorescence assay and immunoblot analysis showed highly reduced levels of ZIKV E protein expressed in infected podocytes pretreated with DWK-1. Also observed was a robust suppression of proinflammatory gene expression, IFN-β (interferon β) RANTES (regulated on activation, normal T cell expressed and secreted), MIP-1α (macrophage inflammatory protein-1α), TNF-α (tumor necrosis factor-α) and IL1-α (interleukin 1-α) in ZIKV-infected podocytes pretreated with DWK-1. Thus, Working Example 2 found that Morpholino DWK-1 targeting the ZIKV 5'-UTR effectively inhibited ZIKV replication and suppressed ZIKV-induced proinflammatory gene expression. Working Example 2 is described in further detail, below, with sections and subsections used for organizational purposes.

Materials and Methods

Morpholino Oligomers

The ZIKV-targeted morpholino oligomer DWK-1 was designed to be complementary to the 25-mer nucleotide sequence within the ZIKV 5' untranslated region (5'-UTR) (bolded in brackets) that includes the first ATG translation start codon (bolded, underlined) of the Zika virus strain PRVABC59 (GenBank mRNA transcript KU501215.1, PRVABC59/Puerto-Rico/2015): 5'-GTA TCA ACA GGT TTT ATT TTG GAT [TTG GAA ACG AGA GTT TCT GGT CATG]AAA AAC CCA AAA AAG AAA TCC G-3' (SEQ ID NO: 10). The 5'-UTR of the ZIKV PRVABC59 RNA sequence targeted by DWK-1 is highly conserved among ZIKV strains. The sequence of DWK-1 complementary to the 25-mer of ZIKV5'-UTR is as follows: 5'-CAT GAC CAG AAA CTC TCG TTT CCA A-3' (SEQ ID NO: 3). The control oligo used in this Example was a standard control oligo that targets a human beta-globin intron mutation that causes beta-thalassemia. This oligo, designated as Co DWK-1, causes little change in phenotype in any known test system except human beta-thalassemic hematopoietic cells and is appropriate negative control for custom vivo-morpholino oligos (Moulton, 2017). The sequence of Co DWK-1 is as follows: 5'-CCT CTT ACC TCA GTT ACA ATT TAT A-3' (SEQ ID NO: 11). Morpholino oligonucleotides used (vivo-morpholinos) were conjugated to a delivery moiety consisting of an eight-branched dendrimer carrying a guanidinium moiety at each branch tip (see FIG. 5) for efficient delivery of morpholino to the cytosol and nuclear compartments of the cell. The vivo-morpholinos DWK-1 and Co DWK-1 were synthesized by Gene Tools, LLC. The rationale for using 25-mers which is the longest commercially available morpholino is that they are recommended for most applications. This is because efficacies increase substantially with increasing length and because long oligos best assure access to a single-stranded region in the target RNA, as is required for nucleation of pairing by the oligo. This length versus activity study was carried out by Gene Tools with morpholino oligos and 25 mers were found to be the optimal length for sequence specific knockdown of genes in mammalian cells.

Cells

Immortalized human glomerular podocytes AB8/13 were obtained from Moin A. Saleem (Saleem et al., 2002) and were cultured as described (Khatua et al., 2010). Cells were trypsinized and plated in 6 well dishes at a concentration $3.5 \times 10^5$ per well. The cells were cultured in RPMI media supplemented with 10% FCS and insulin-transferrin-selenium (ITS; ThermoFisher Scientific).

Morpholino Pretreatment

Lyophilized morpholino oligos DWK-1 and Co-DWK-1 were dissolved in sterile water to a final concentration of 0.5 mM. A 30 µL aliquot was added to podocytes cultured in fresh 1.5 mL RPMI media supplemented with 10% FCS and ITS per well of 6-well dishes. The final concentration of DWK-1 and Co DWK-1 in culture medium was 10 µM. After 24 h incubation, podocytes were rinsed with culture medium and either mock infected or infected with ZIKV and cultured for the indicated time in the absence of morpholinos.

ZIKV Preparation and Titration

The Zika virus strain PRVABC59 used in this study was originally isolated from a human serum specimen from Puerto Rico in December 2015, nucleotide (GenBank): KU501215 ZIKV strain PRVABC59, complete genome (Lanciotti et al., 2015; Thomas et al., 2016; Dirlikov et al., 2016; Lancontti et al., 2008). The virus was cultivated in Vero cells and infectious supernatant was filtered using a 0.22 µm filter and the serum content adjusted to 15%. Stock viral titers were determined as previously described (Alcendor, 2017). All experiments were carried out under biosafety level-2 containment as recommended. Use of ZIKV was approved by the Meharry Medical College Institutional Review Board and the Institutional Biosafety Committee.

ZIKV RNA Analysis

Total cellular RNA was isolated from the cells using Quick RNA MiniPrep kit (Zymo Research) and 500 ng RNA was reverse transcribed into cDNA using iScript cDNA synthesis kit (Bio-Rad). Real-time PCR was performed on CFX96 PCR machine (Bio-Rad) using SYBR Green PCR master mix (Bio-Rad), ZIKA specific primers (forward primer 5'-CCG CTG CCC AAC ACA AG-3' (SEQ ID NO: 12) and reverse primer 5'-CCA CTA ACG TTC TTT TGC AGA CAT-3' (SEQ ID NO: 13)) and GAPDH specific primers (forward 5'-GAA GGT GAA GGT CGG AGT-3' (SEQ ID NO: 8) and reverse 5'-GAA GAT GGT GAT GGG ATT TC-3' (SEQ ID NO: 9)). The following amplification conditions were used: 95° C. for 3 min for initial denaturation and 40 cycles of 95° C. for 10 s and 60° C. for 45 s. Samples were analyzed in triplicate and ZIKV RNA expression was normalized to GAPDH mRNA levels. Data are presented as mean±SD. A standard curve was generated by using the 10-fold serial dilutions of a synthetic ZIKV RNA (ATCC VR-3252SD) with known ZIKV genome copies (provided as $1.2 \times 10^6$ copies/µL). Absolute quantification of ZIKV genome copy numbers was carried out in triplicate by comparing each sample's threshold cycle (CT) value with a ZIKV RNA standard curve.

qRT-PCR Analysis of the Proinflammatory Cytokine Gene Expression

Total cellular RNA was isolated, processed, and analyzed as described above. The primers used to analyze cytokine gene expression are as follows: IFN-β: forward 5'-CTT GGA TTC CTA CAA AGA AGC AGC-3' (SEQ ID NO: 14), reverse 5'-TCC TCC TTC TGG AAC TGCT GCA-3' (SEQ ID NO: 15); RANTES: forward 5'-CCT GCT GCT TTG CCT ACA TTG C-3' (SEQ ID NO: 16), reverse 5'-ACA CAC TTG GCG GTT CTT TCG G-3' (SEQ ID NO: 17); MIP-1α: forward 5'-ACT TTG AGA CGA GCA GCC AGT G-3' (SEQ ID NO: 18), reverse 5'-TTT CTG GAC CCA CTC CTC ACT G-3' (SEQ ID NO: 19); TNF-α: forward 5'-CTC TTC TGC CTG CTG CAC TTT G-3' (SEQ ID NO: 20), reverse 5'-ATG GGC TAC AGG CTT GTC ACT C-3' (SEQ ID NO: 21); IL-1α: forward 5'-TGT ATG TGA CTG CCC AAG ATG AAG-3' (SEQ ID NO: 22), reverse 5'-AGA GGA GGT TGG TCT CAC TAC C-3' (SEQ ID NO: 23); IL-6: forward 5'-AGA CAG CCA CTC ACC TCT TCA G-3' (SEQ ID NO: 24), reverse 5'-TTC TGC CAG TGC CTC TTT GCT G-3' (SEQ ID NO: 25).

Samples were analyzed in triplicate and cytokine gene expression was normalized to GAPDH mRNA levels.

Immunofluorescence

Immunofluorescent staining was performed as previously described (Alcendor, 2017). Briefly, chamber slide cultures containing mock infected human podocytes, podocytes infected with ZIKV, and podocytes infected ZIKV after 24 hours pre-treatment with DWK-1. Cells were washed twice with PBS pH 7.4, air dried, and fixed in absolute methanol for 20 min at −20° C. Cells were air dried for 10 min, hydrated in Tris buffered saline (pH 7.6) for 10 min, and incubated for 1 h with the 4G-2 Flavivirus group antigen monoclonal antibodies from Millipore (Temecula, Calif., USA) at a dilution 1:100 in PBS pH 7.4. (Wilkerson et al., 2015).

Western Blot Analysis

Cell extracts were prepared using RIPA lysis buffer [50 mM Tris pH 7.5, 150 mM NaCl, 2 mM ethylenediaminetetraacetic acid (EDTA) pH 8.0, 1% NP40, 0.5% sodium deoxycholate, 0.1% sodium dodecyl sulfate (SDS), and proteinase inhibitor (Complete Ultra, Roche). Lysates were incubated on ice for 30 min and then clarified by centrifugation. Total protein was measured by micro BCA protein assay kit (ThermoFisher Scientific). Protein lysates (30 µg) were separated by 10% SDS-PAGE, transferred to nitrocellulose membranes (Bio-Rad), blocked with 5% milk in 0.1% TBST (0.1% Tween 20, 20 mM Tris, 150 mM NaCl) and incubated at 4° C. overnight with 4G-2 Flavivirus group antigen monoclonal antibody (Millipore, Temecula, Calif., USA) at 1:250 dilution. Synaptopodin antibody (Santa Cruz Biotechnology) was used at 1:250 dilution and GAPDH antibody (Santa Cruz Biotechnology) at 1:3000 dilution. Membranes were washed five times in 0.1% TBST and incubated for one hour with corresponding secondary antibody conjugated with HRP (ThermoFisher Scientific) at a dilution of 1:50,000. Immunoreactive bands were detected with WesternBright ECL (Advansta) following exposure to X-ray film.

Statistical Analysis

Experiments presented in this study were performed independently three times under similar conditions. Data are presented as means with standard deviations. Unpaired t-test was used to compare the mean values between groups. Differences were considered statistically significant at $P<0.05$.

Results

Figures 6, 7:
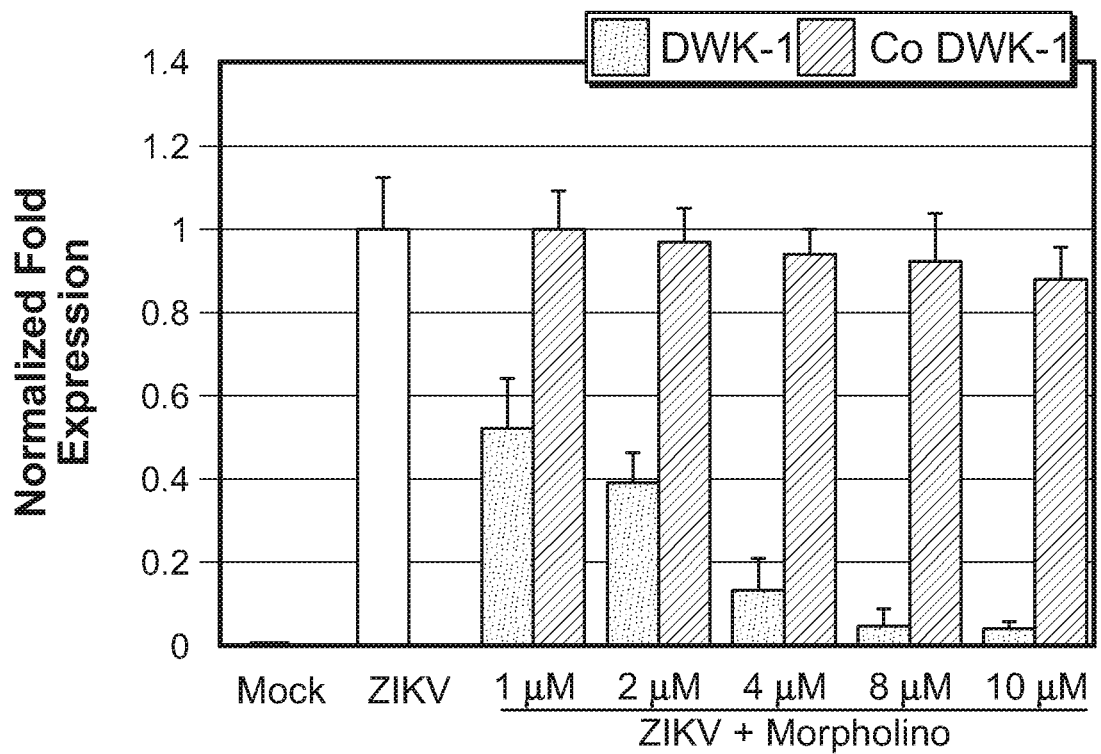
FIG. 6: Dose-dependent effect of DWK-1 and Co DWK-1 on the accumulation of intracellular ZIKV RNA in infected human podocytes. Podocytes were pretreated for 24 h with the indicated doses of DWK-1 or Co DWK-1, rinsed and infected with ZIKV at MOI of 0.1 in the absence of morpholinos. Total RNA was isolated from the mock infected and ZIKV-infected cells at 72 h p.i. Expression of ZIKV RNA was determined by qRT-PCR and normalized to GAPDH mRNA expression. ZIKV infections were performed in triplicate. Values represent mean±SD.
FIG. 7: Mortality of CD-1 mice 96 h after subcutaneous injection of DWK-1.

DWK-1 Inhibits Accumulation of Intracellular ZIKV RNA in a Dose-Dependent Manner To determine an effective concentration of vivo-morpholino DWK-1 (FIG. 5) that inhibits ZIKV replication in human podocytes, the cells were pretreated for 24 h with various concentrations of DWK-1 and Co DWK-1 ranging from 1 to 10 µM, rinsed and mock infected or infected with ZIKV (PRVABC59) at a multiplicity of infection (MOI) of 0.1 in the absence of morpholinos. Seventy two hours after infection, the cells were collected and intracellular ZIKV RNA accumulation was determined by qRT-PCR (FIG. 6). Results show that DWK-1 reduced intracellular ZIKV RNA accumulation in a dose-dependent concentration with about 50% inhibition of ZIKV RNA accumulation at 1.0-1.5 µM and >95% inhibition at 10 µM. In contrast, Co-DWK-1 shows only a small inhibition (9±5%) at 10 µM. Since 10 µM concentration of DWK-1 was of low toxicity to the cells, it was used in all Working Example 2 experiments.

DWK-1 Reduces Expression of Intracellular ZIKV RNA in Podocytes

Figure 8A:
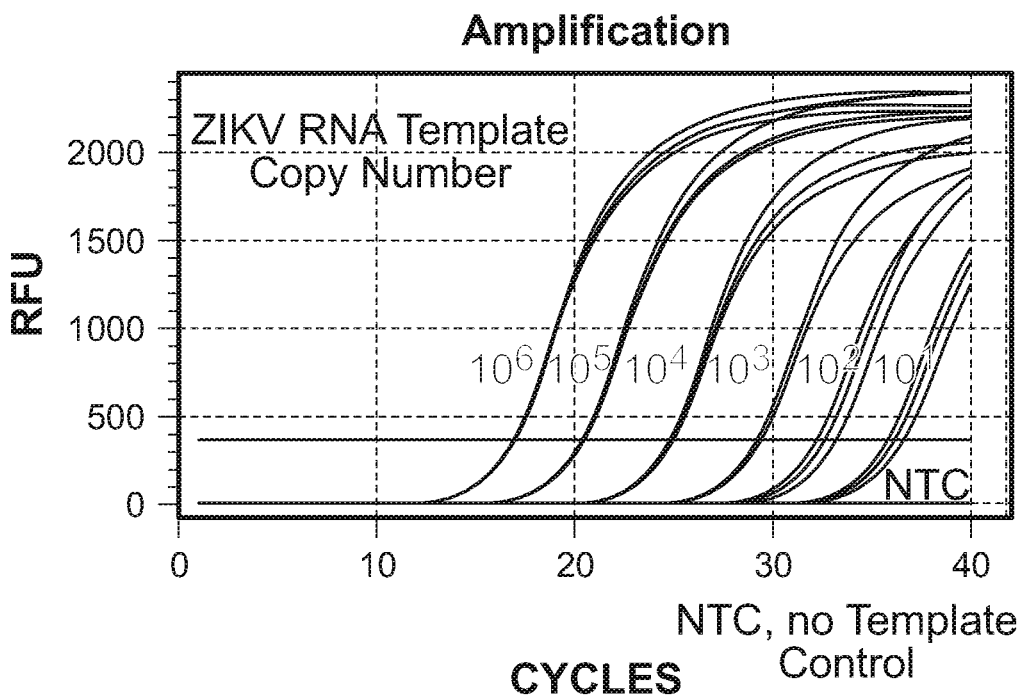
FIGS. 8A-8D: DWK-1 reduces ZIKV RNA genome copy number in infected podocytes. (8A) Ten-fold dilutions of synthetic ZIKV RNA (VR-3252SD, $10^6$ to 10 copies) were amplified by qRT-PCR using ZIKV specific primers. Amplification curves are shown. NTC, no template control. (8B) The regression line was established by plotting the threshold cycles (CT) values against the copy number of synthetic RNA. The coefficient of determination $R^2$ was 0.997 and slope was −3.923. (8C) Total cellular RNA isolated from mock, ZIKV infected cells, c controls. Total RNA was isolated at 72 h p.i. and intracellular ZIKV RNA was quantitated by qRT-PCR and normalized to GAPDH mRNA levels. Results show inhibitory effect of DWK-2 on the expression of ZIKV induced (14A) IL-6, (14B) IL-1α, (14C) INF-β, (14D) RANTES genes. Values represent mean±SD of 3 independent samples. The expression of cytokine genes mRNA in mock infected cells was set as 1.0.
Figure 8B:
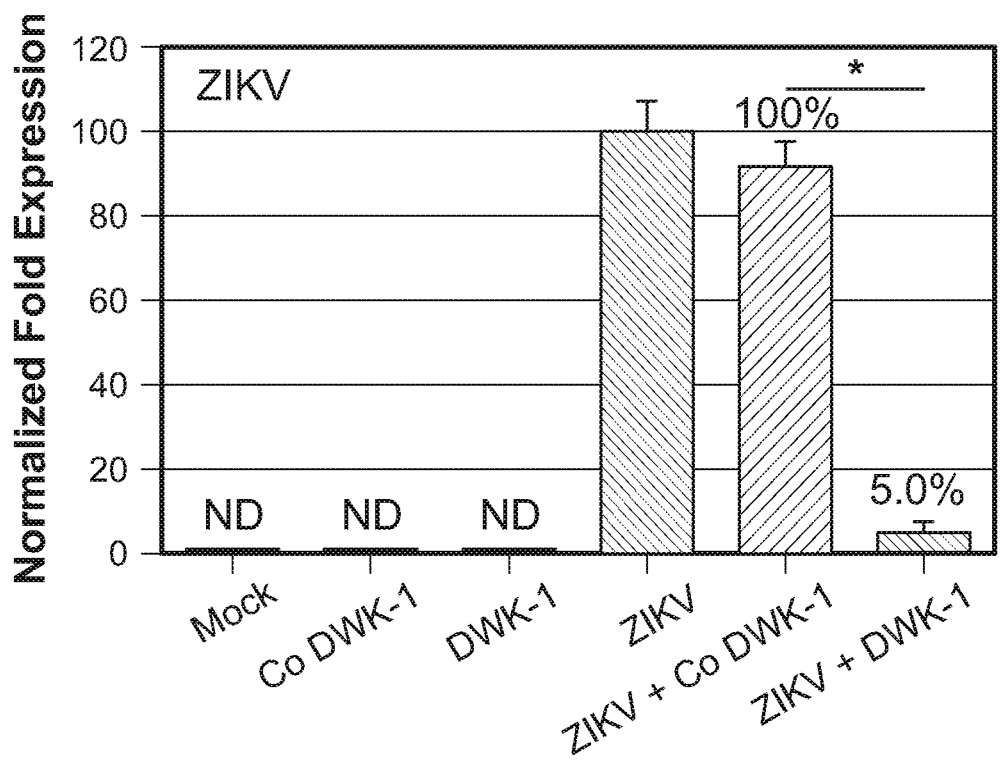
Figure 8C:
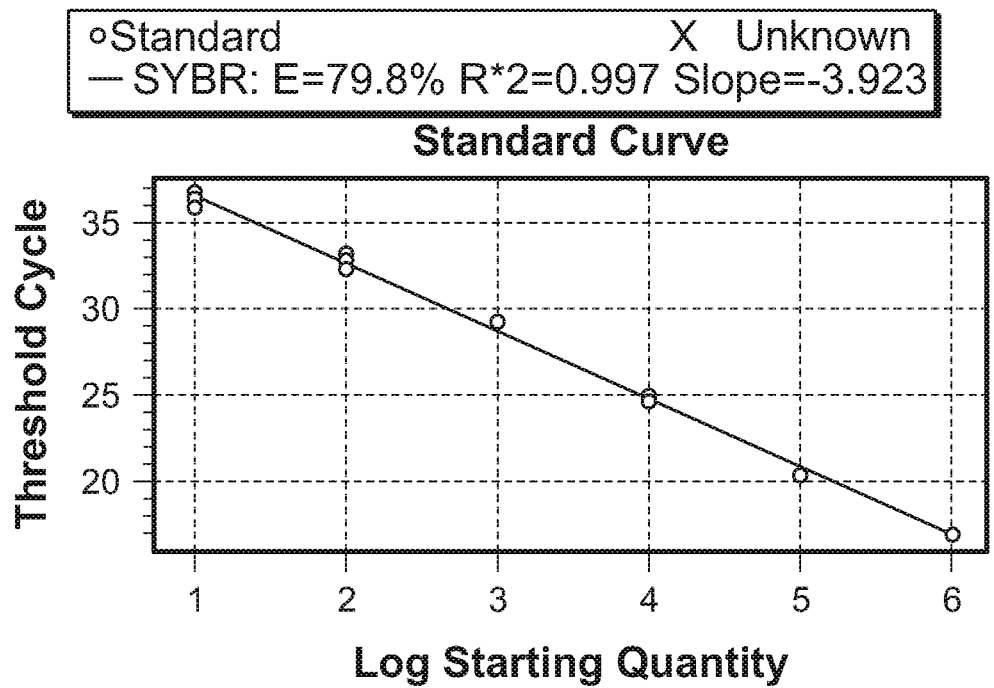
Figure 8D:
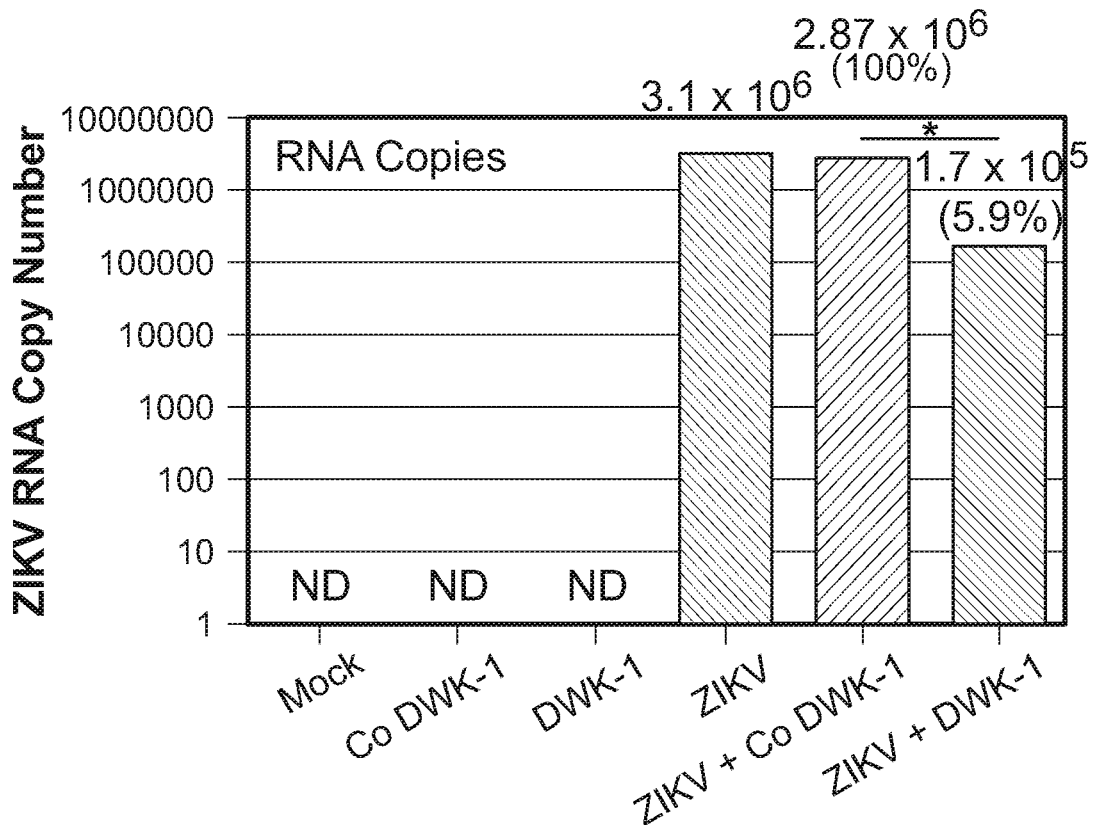

To validate further the antiviral activity of DWK-1, ZIKV RNA copy number was measured in infected podocytes or podocytes pretreated with DWK-1 or Co DWK-1 and subsequently infected with ZIKV. First, a standard curve was generated by using 10-fold dilutions of synthetic ZIKV RNA (ATCC VR-3252SD) (FIG. 8A). The standard curve covered a linear range from $10^6$ to 10 copies of ZIKV RNA with a slope=-3.923 and $R^2$=0.997, indicating a good sensitivity of the SYBR Green qRT-PCR assay (FIG. 8B). Total cellular RNA was isolated from podocytes treated as indicated in FIG. 8C and analyzed by qRT-PCR for the expression of ZIKV and GAPDH transcripts. Results demonstrate 95% reduction of ZIKV RNA expression in podocytes pretreated with DWK-1 and infected for 48 h with ZIKV, as compared to infected podocytes pretreated with Co DWK-1. These results correlated with an about 94% reduction of ZIKV RNA copy number (FIG. 8D) as quantitated from a standard curve (FIG. 8B) generated using synthetic ZIKV RNA.

DWK-1 Strongly Reduces Expression of ZIKV E Protein in Infected Podocytes

Figure 10:
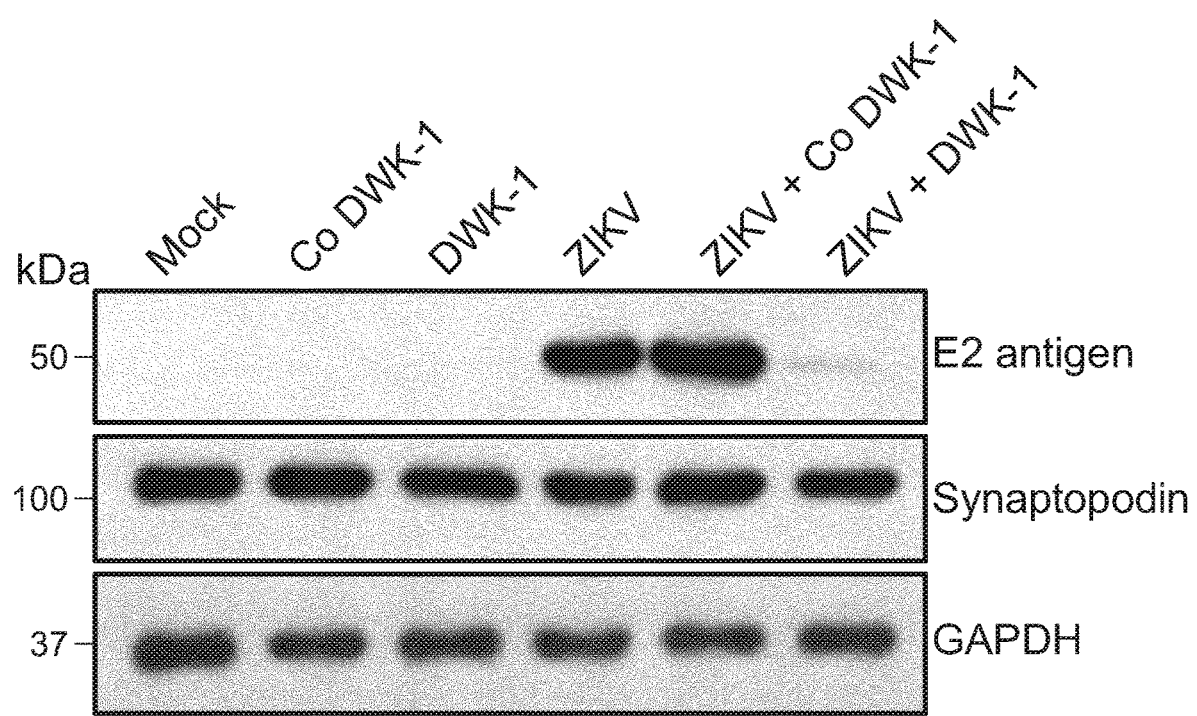

To determine if DWK-1 inhibition of ZIKV transcription in infected human glomerular podocytes results in a decrease in ZIKV protein expression, expression of ZIKV E protein in podocytes pretreated with DWK-1 was examined. Immunofluorescent staining showed that E protein-specific 4G-2 antibody does not stain mock infected podocytes, while podocytes infected with ZIKV for 72 h showed characteristic perinuclear staining with the 4G-2 antibody (FIGS. 9A-9D). In contrast, podocytes pretreated with DWK-1 and infected with ZIKV for 72 h showed only a minimal, if any, expression of ZIKV E protein as compared to mock and isotype controls (FIG. 9A-9D). Similarly, expression of ZIKV E protein in infected podocytes after pretreatment with DWK-1 (ZIKV+DWK-1) was strongly reduced (>98%) by immunoblot analysis (FIG. 10). No E protein expression was observed in uninfected (Mock, Co DWK-1, DWK-1) podocytes. Expression of the podocyte biomarker Synaptopodin was demonstrated not to be significantly affected by ZIKV infection or podocyte exposure to DWK-1 or Co DWK-1 (FIG. 10).

DWK-1 Inhibits ZIKV-Induced Proinflammatory Gene Expression in Podocytes

Figure 11A:
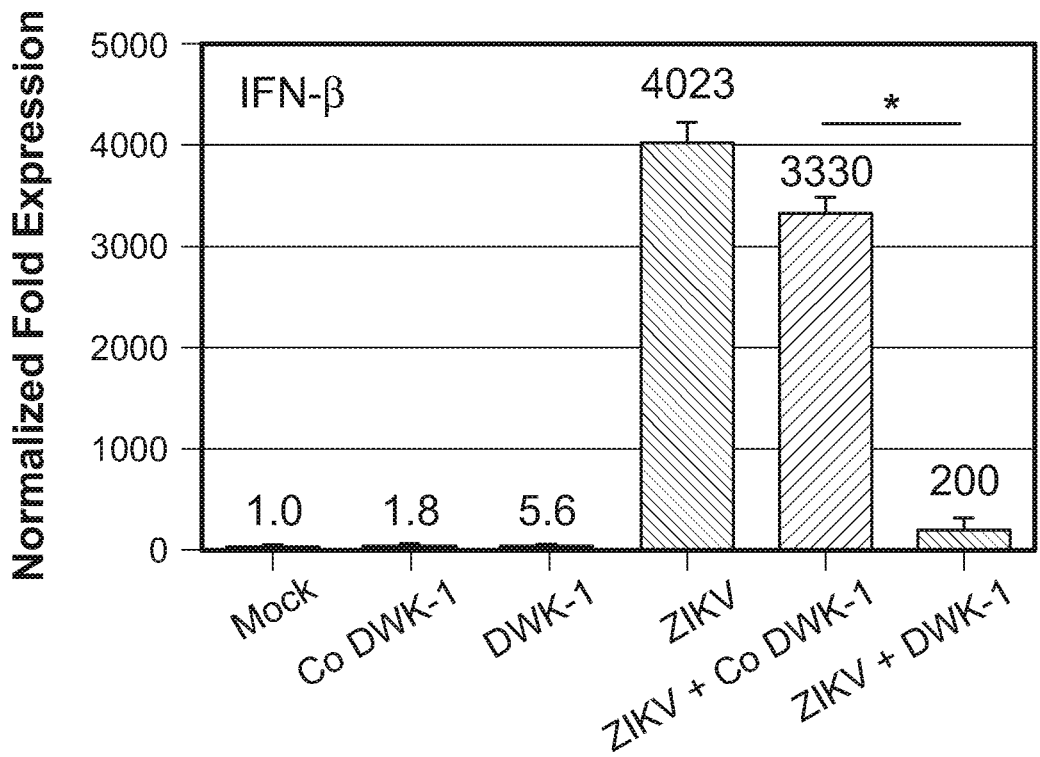
Figure 11B:
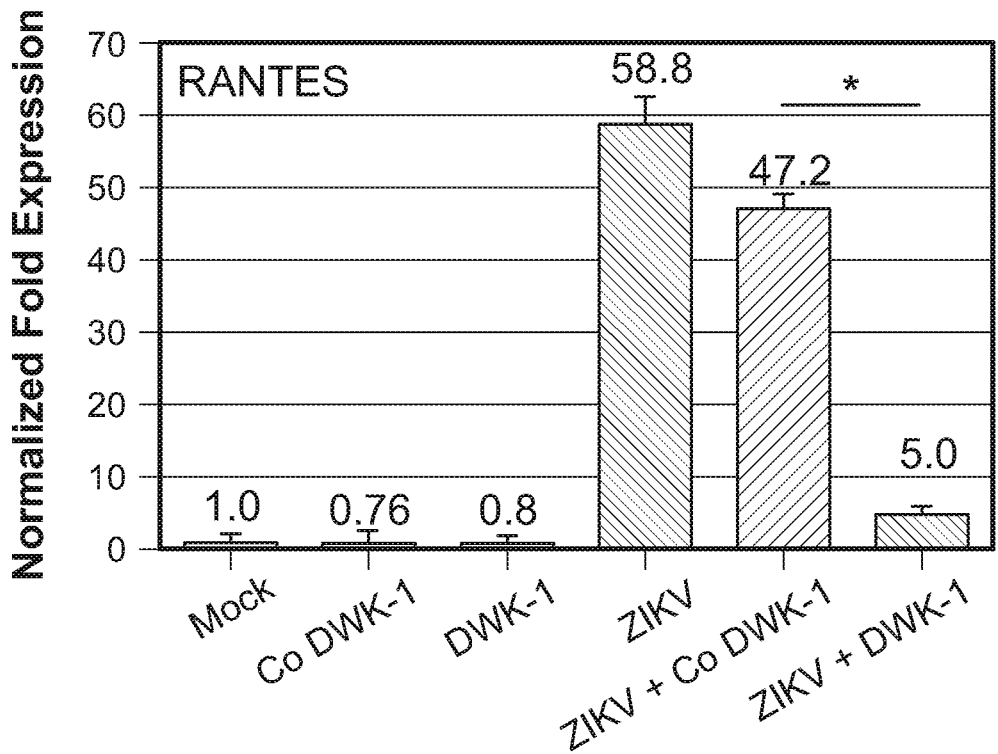
Figure 11C:
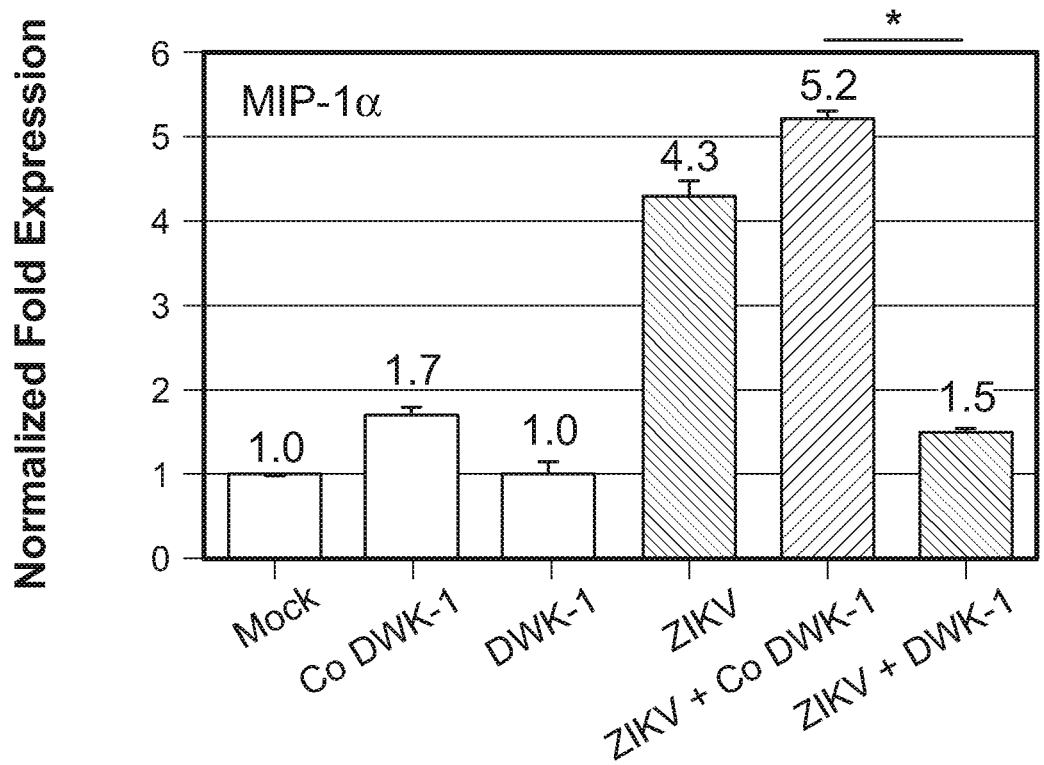
Figure 11D:
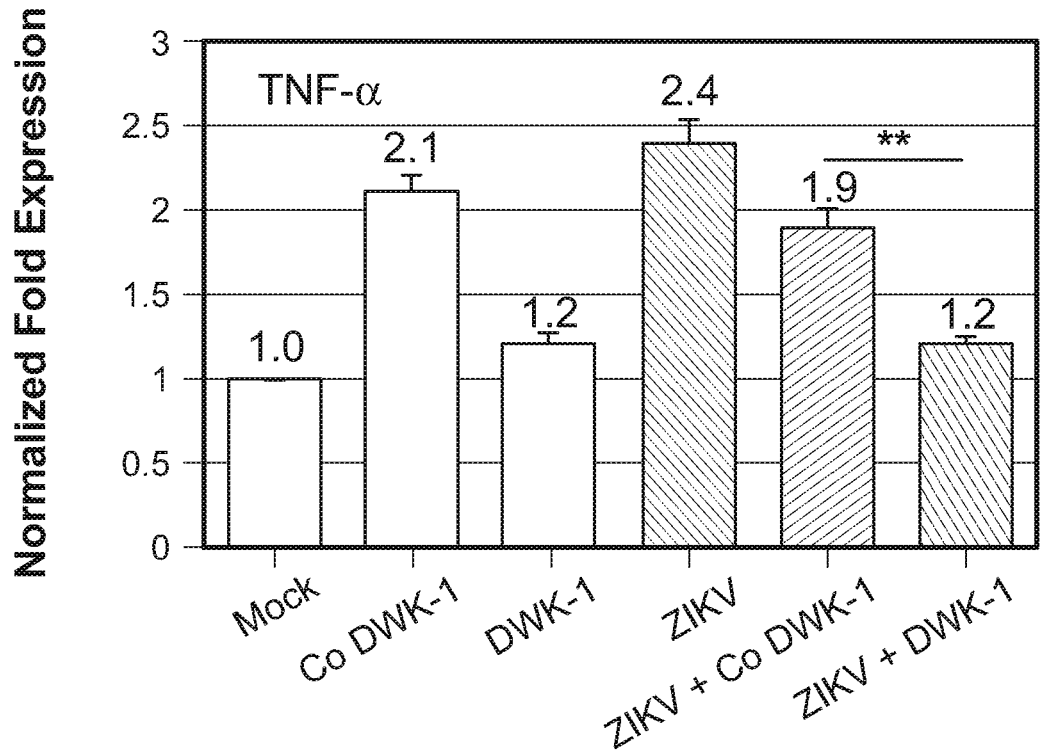
Figure 11E:
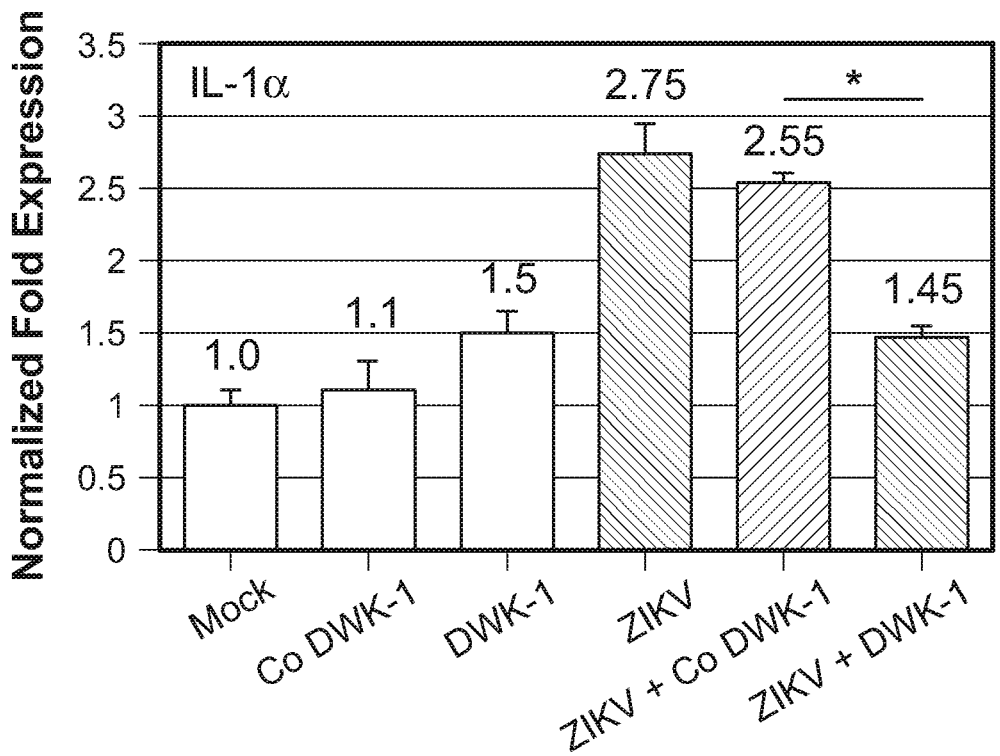
Figure 11F:
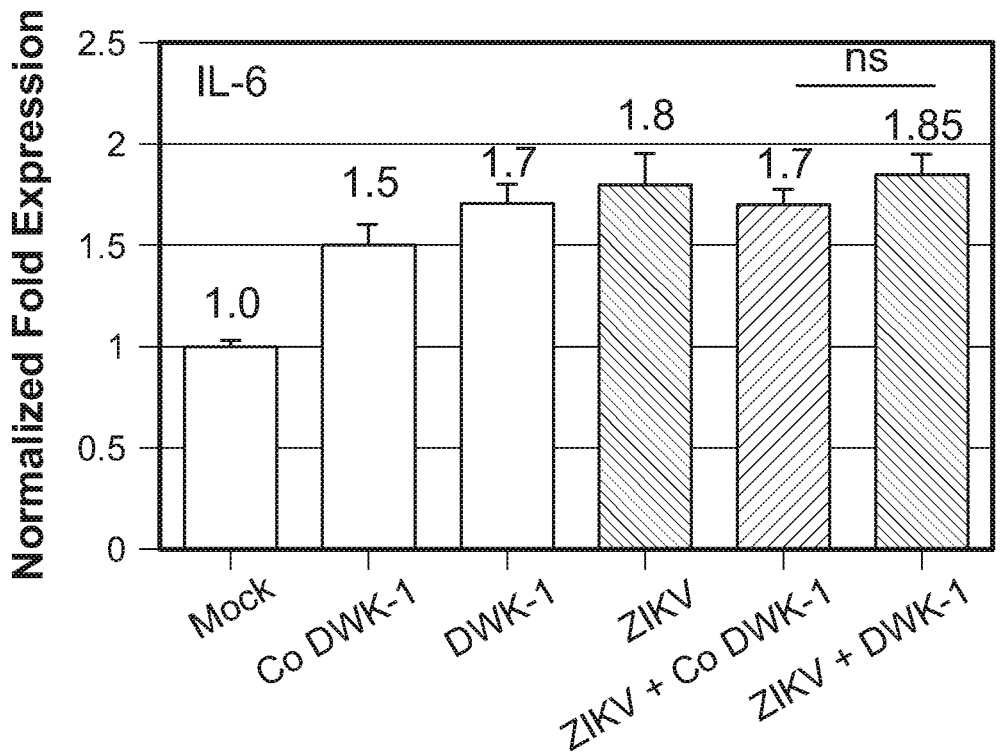

ZIKV virus infection leads to the induction of proinflammatory cytokines. It was examined whether DWK-1 pretreatment affects expression of proinflammatory cytokine genes in ZIKV infected podocytes (FIGS. 11A-11D). Surprisingly, ZIKV induced a robust 4,023-fold increase in IFN-β gene expression and 3,330-fold increase in podocytes pretreated with Co DWK-1 (FIG. 11A), when compared to mock infected cells. Importantly, pretreatment with DWK-1 prior to ZIKV infection resulted in over a 16-fold suppression of IFN-β transcriptional expression, as compared to cells pretreated with Co DWK-1 (FIG. 11A). Similarly, a strong upregulation of RANTES transcriptional expression at 72 h after infection with ZIKV (58.8-fold increase) and in cells pretreated with Co DWK-1 and infected with ZIKV (47.2-fold increase) (FIG. 11B) was observed. Pretreatment of podocytes with DWK-1 prior to ZIKV infection resulted in >9-fold reduction in RANTES gene expression, when compared to levels detected in infected podocytes pretreated with Co DWK-1 (FIG. 11B). No significant changes in the RANTES transcriptional expression were observed in mock podocytes or podocytes exposed to the DWK-1 or Co DWK-1 alone (FIG. 11B). Although the expression of MIP-1 α, TNF-α and IL-1α was not so potently induced by ZIKV in podocytes (~2 to 4-fold upregulation) when compared to IFNβ or RANTES, pretreatment with DWK-1 prior to ZIKV infection reduced expression of these genes to levels detected in mock infected podocytes (FIGS. 11C-11E). No significant changes in IL-6 transcriptional expression were detected in podocytes exposed to DWK-1 prior to ZIKV infection, when compared to infected podocytes pre-exposed to Co DWK-1 (FIG. 11F).

Discussion

In this Working Example, the effectiveness of the ZIKV targeted morpholino DWK-1 was demonstrated to suppress active transcription of ZIKV in vitro by approximately 95% and to reduce ZIKV E protein expression to undetectable levels. In addition, it was shown that DWK-1 has no effect on the steady state expression levels of the podocyte specific biomarker synaptopodin. It was also shown that DWK-1 potently reduced expression of IFN-β, RANTES, MIP-1α and TNF-α in ZIKV infected cells, as compared to infected cells pretreated with Co DWK-1.

Advantageously, the antiviral agents described herein have the potential to be highly useful as prophylaxis or treatment for immunosuppressed SOTp receiving allografts from ZIKV infected donors as well as an ant-infective for protecting a blood supply tainted with ZIKV especially in ZIKV endemic regions where ZIKV screening of blood is unavailable.

These antivirals agents, which inhibit active replication of ZIKV, would be beneficial for these patients and could potentially suppress sporadic outbreaks of ZIKV infection in the general population. Such an antiviral agent that is stable at room temperature could be highly useful in arid conditions without refrigeration. This advantage could also enable development of a carry-on intervention to prevent ZIKV infection for military personnel and humanitarian workers traveling to ZIKV endemic regions.

Conclusions

The vivo-morpholino is composed of a morpholino oligo with a unique covalently linked delivery moiety, which is comprised of an octa-guanidine dendrimer. The active component, namely the arginine rich delivery peptides of the guanidinium group facilitates delivery of the modified morpholino into the cytosol. In this Working Example, a morpholino-based antiviral was shown to target ZIKV 5'-UTR, be of low-toxicity, be stable at room temperature, and is capable of penetrating target cells.

REFERENCES

Alcendor D J, Zika Virus Infection of the Human Glomerular Cells: Implications for Viral Reservoirs and Renal Pathogenesis. J Infect Dis 2017 jix171. doi: 10.1093/infdis/jix171

Dirlikov E, Ryff K R, Torres-Aponte J, et al. 2016. Update: Ongoing Zika Virus Transmission—Puerto Rico, Nov. 1, 2015-Apr. 14, 2016. MMWR Morb Mortal Wkly Rep 2016; 17:451-55.

Khatua A K, Taylor H E, Hildreth J E, et al. Non-productive HIV-1 infection of human glomerular and urinary podocytes. Virology 2010; 1:119-27.

Lanciotti, R. S., Kosoy, O. L., Laven, et al. Genetic and serologic properties of Zika virus associated with an epidemic, Yap State, Micronesia, 2007. Emerg Infect Dis 2008; 14: 1232-39.

Lanciotti R S, Lambert A J, Holodniyet M, et al. 2016. Phylogeny of Zika Virus in Western Hemisphere, 2015. Emerg Infect Dis 2016; 5: 933-35.

Moulton J D. Using morpholinos to control gene expression. Curr. Protoc. Nucleic Acid Chem. 2017; 68:4.30.1-4.30.29.

Saleem M A, O'Hare M J, Reiser J, et al. A conditionally immortalized human podocyte cell line demonstrating nephrin and podocin expression. J Am Soc Nephrol 2002; 3:630-8.

Thomas D L, Sharp T M, Torres J, et al. Local Transmission of Zika Virus—Puerto Rico, Nov. 23, 2015-Jan. 28, 2016. MMWR Morb Mortal Wkly Rep 2016; 6:154-58.

G. Working Example 3

Figure 12:
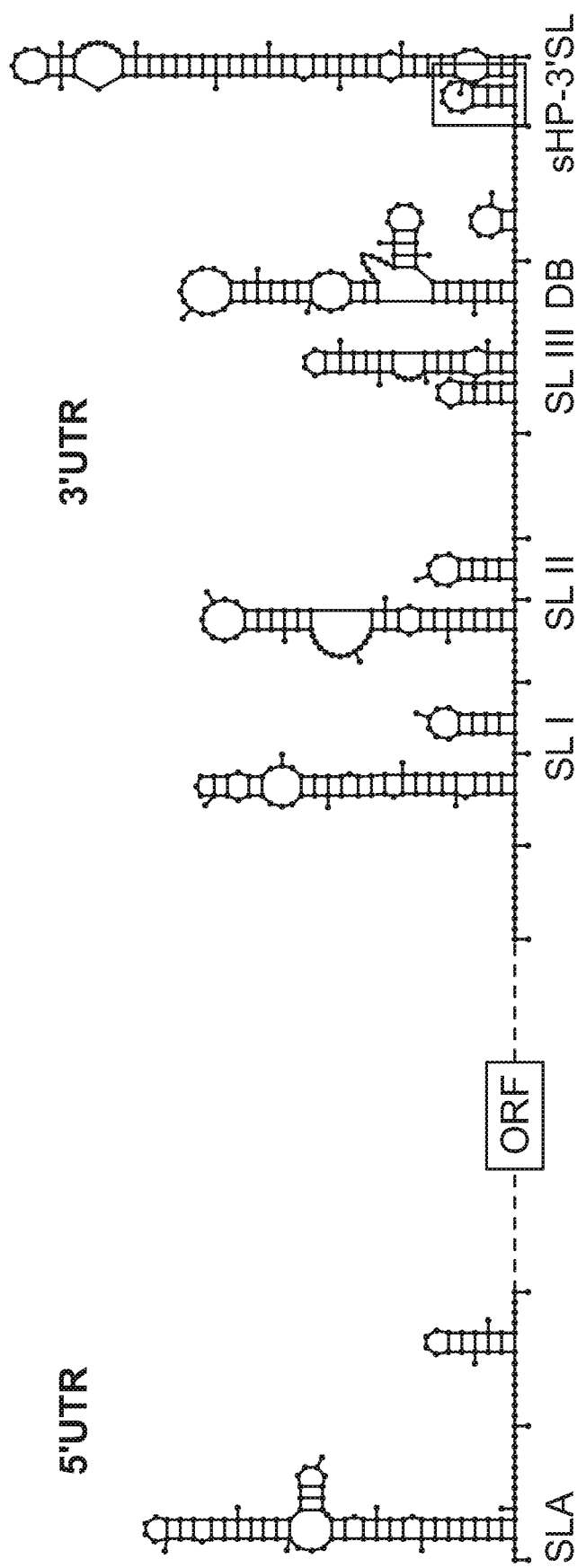
Figure 14A:
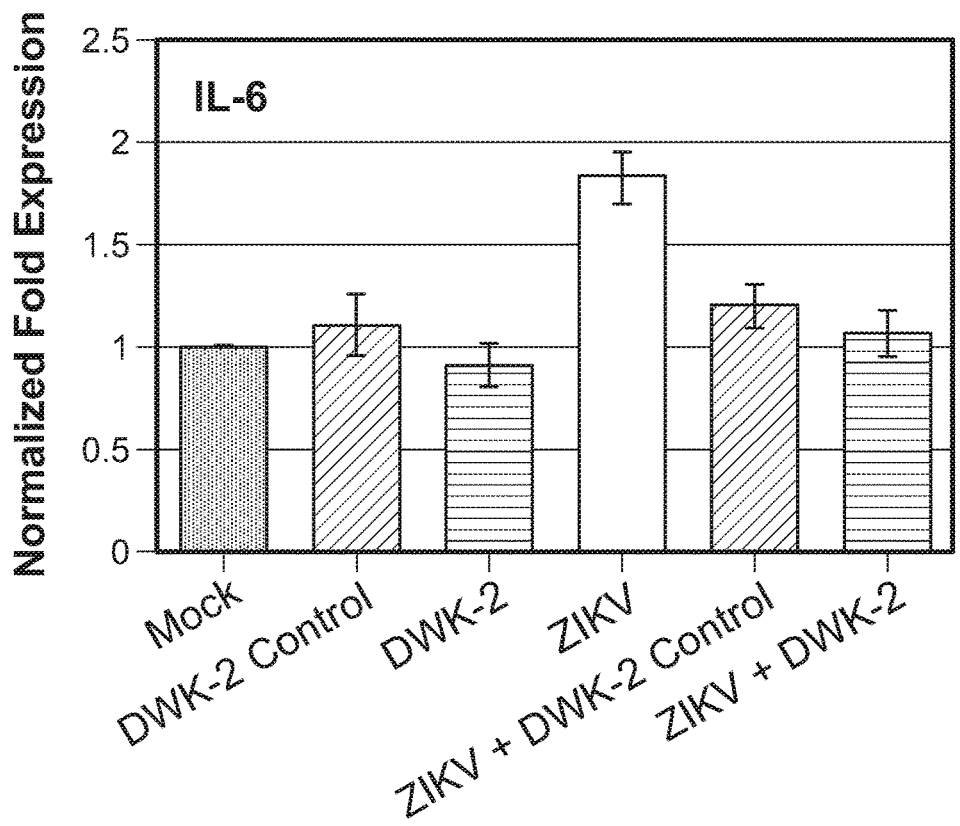
Figure 14B:
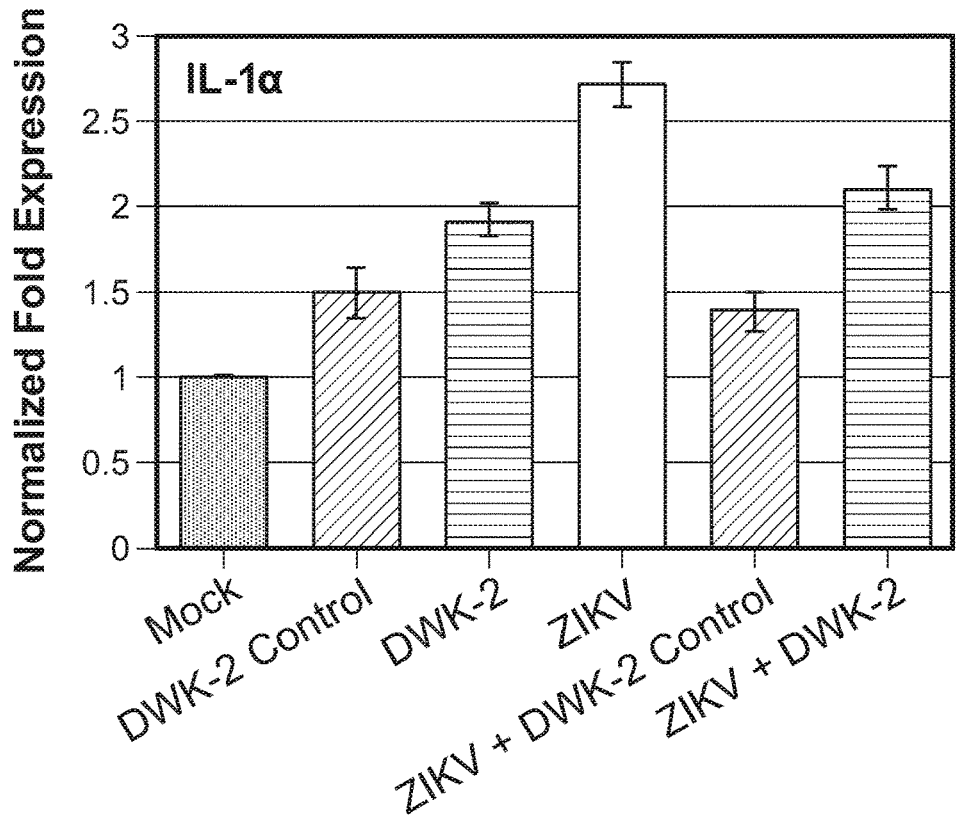
Figure 14C:
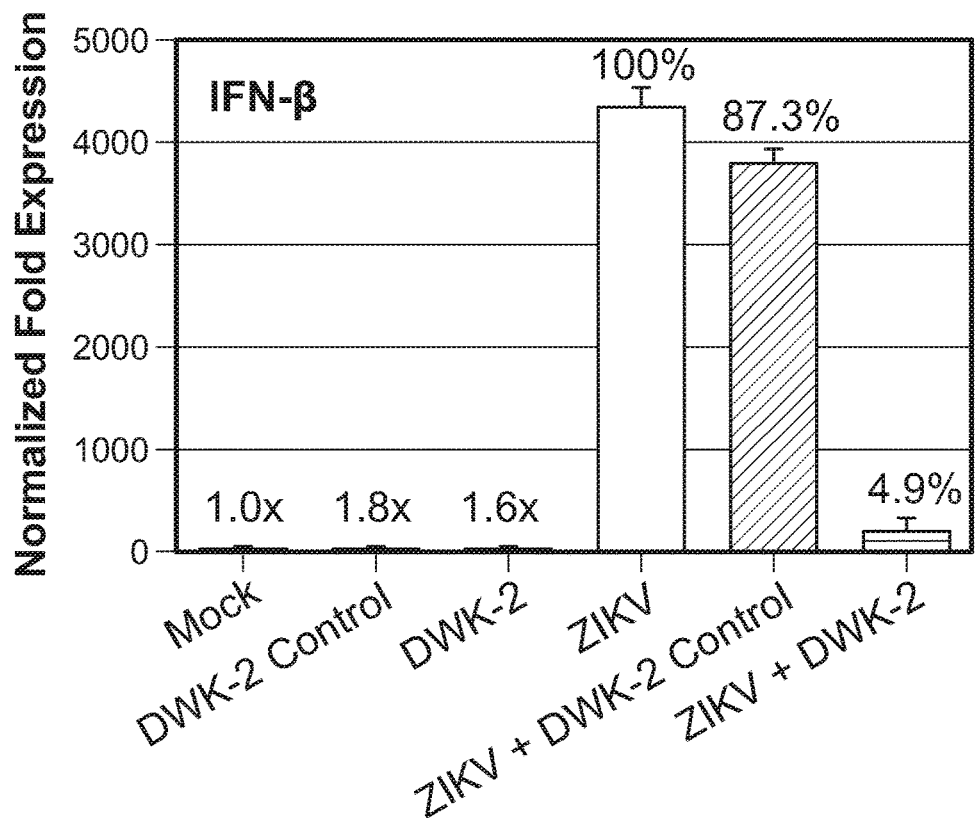
Figure 14D:
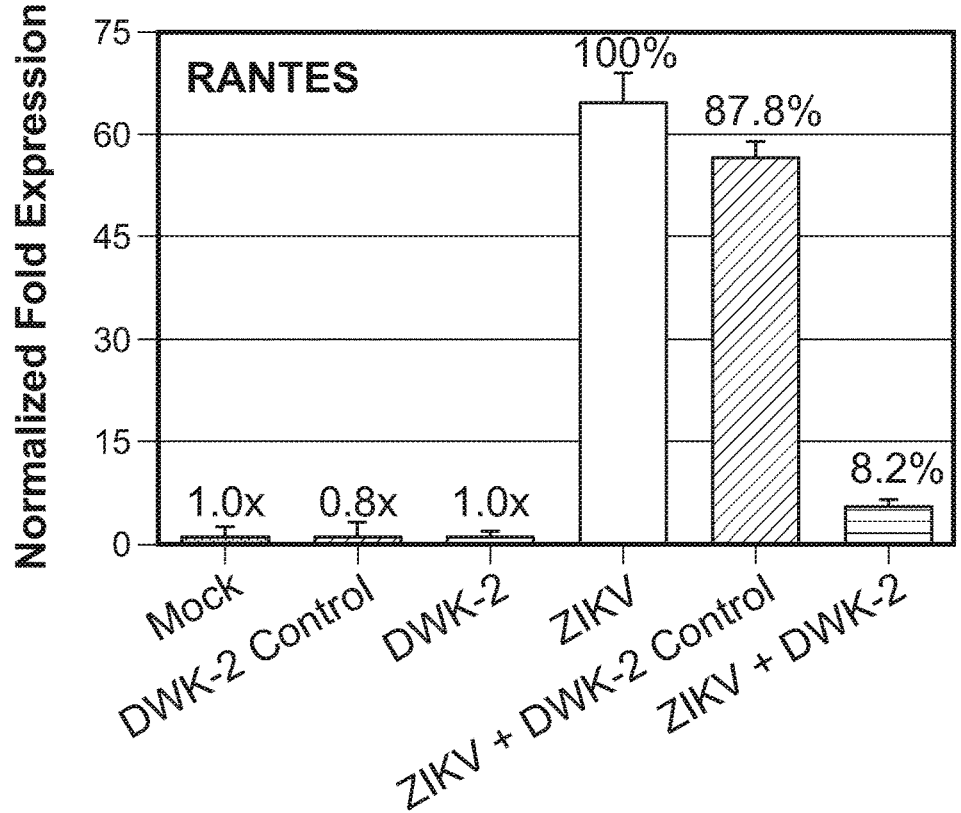

An MPO was designed that targets a sequence in the sHP-3'SL region of the 3'UTR of ZIKV strains. This is a highly conserved region (FIGS. 12 and 13). The MPO, designated DWK-2, targets the sequence 5'-GCT GGG AAA GAC CAG AGA CTC CAT G-3' (SEQ ID NO: 4) (FIG. 13), and has the primary sequence 5'-CAT GGA GTC TCT GGT CTT TCC CAG C-3' (SEQ ID NO: 5).

The inhibition of ZIKV-induced proinflammatory cytokine gene expression by DWK-2 was measured. Podocytes were pretreated for 24 h with 10 µM DWK-2 or Co DWK-1 (control) and infected with ZIKV. Mock infected cells and cells treated only with DWK-2 or Co DWK-2 were included as controls. Total RNA was isolated at 72 h p.i. and intracellular ZIKV RNA was quantitated by qRT-PCR and normalized to GAPDH mRNA levels. Results in FIGS. 14A-14D show inhibitory effect of DWK-2 on the expression of ZIKV induced (FIG. 14A) IL-6, (FIG. 14B) IL-1α, (FIG. 14C) INF-β, and (FIG. 14D) RANTES genes. Values represent mean±SD of 3 independent samples. The expression of cytokine genes mRNA in mock infected cells was set as 1.0.

Figure 15A:
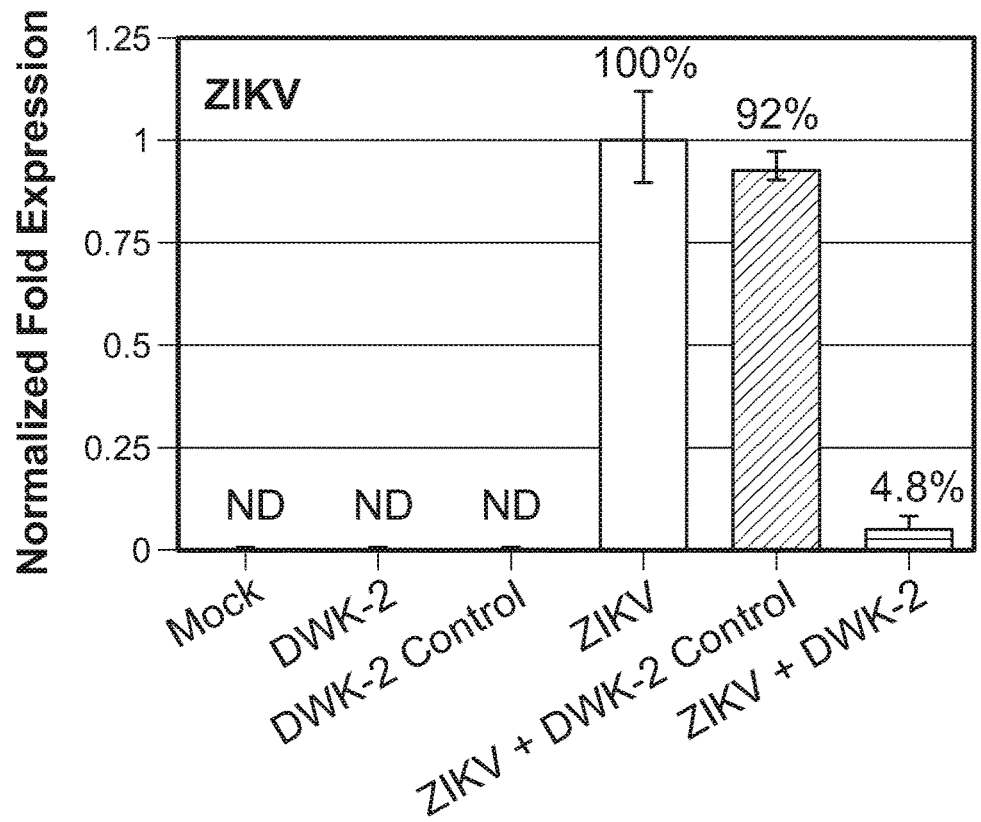
FIGS. 15A-15B: (15A) DWK-2 inhibits accumulation of intracellular ZIKV RNA in infected podocytes. Podocytes were pretreated for 24 h with 10 µM DWK-2 or Co DWK-2 (control) and infected with ZIKV. Mock infected and DWK-2 and Co DWK-2 pretreated cells were included as controls. Total RNA was isolated at 72 h p.i. and intracellular ZIKV RNA expression was determined by qRT-PCR and normalized to GAPDH mRNA levels. ZIKV infections were performed in triplicate. Values represent mean±SD of 3 independent samples. ND, not detected. (15B) DWK-2 reduces ZIKV RNA genome copy number in infected podocytes. Total cellular RNA isolated from mock, ZIKV infected cells, or cells pretreated for 24 h with 10 µM DWK-2 alone, or from DWK-2 pretreated cells and infected with ZIKV for 48 h was analyzed by qRT-PCR for the expression of ZIKV and GAPDH RNA. Relative expression of intracellular ZIKV RNA normalized to GAPDH RNA is reduced by 94.2%. Quantitation of ZIKV genome copy number in total intracellular RNA shows a reduction in ZIKV copy number in infected cells pretreated with DWK-2. Values represent mean±SD of 3 independent samples. ND, not detected.

The inhibition of accumulation of intracellular ZIKV RNA in infected podocytes was measured. Podocytes were pretreated for 24 h with 10 µM DWK-2 or Co DWK-2 (control) and infected with ZIKV. Mock infected and DWK-2 and Co DWK-2 pretreated cells were included as controls. Total RNA was isolated at 72 h p.i. and intracellular ZIKV RNA expression was determined by qRT-PCR and normalized to GAPDH mRNA levels. ZIKV infections were performed in triplicate. Results are shown in FIG. 15A. Values represent mean±SD of 3 independent samples. ND, not detected.

Figure 15B:
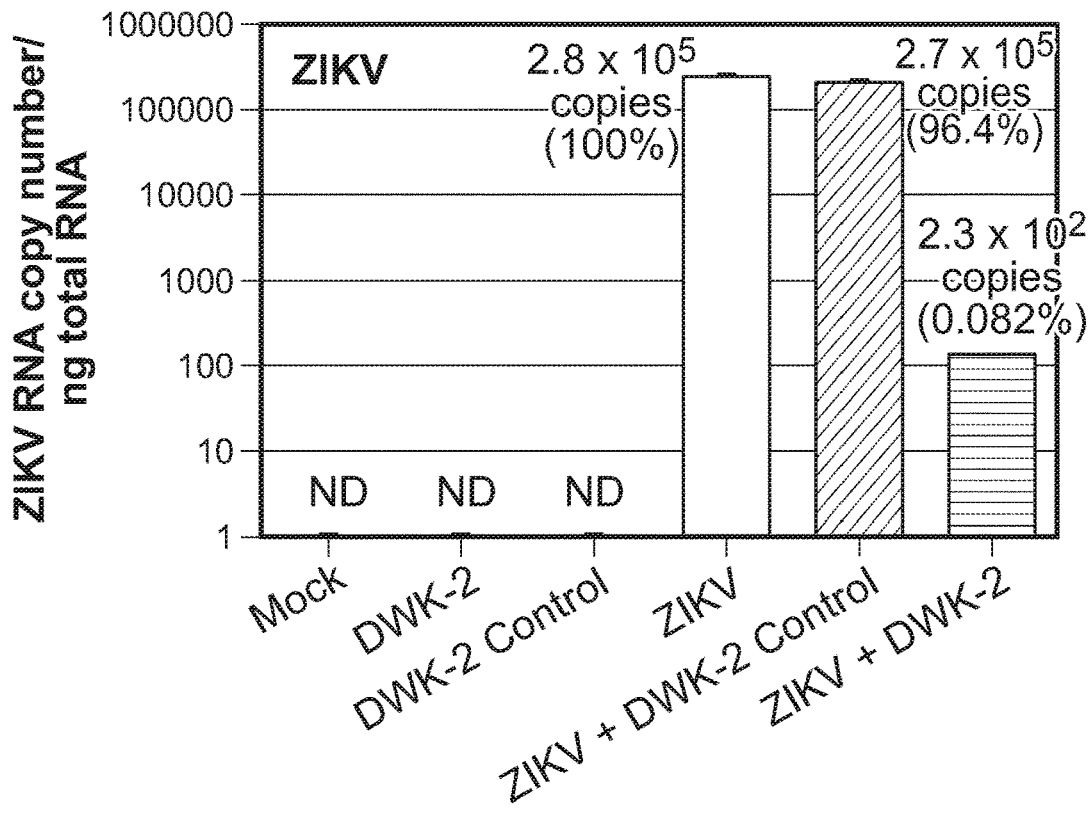

The effect of DWK-2 on ZIKV RNA genome copy number in infected podocytes was tested. Total cellular RNA isolated from mock, ZIKV infected cells, or cells pretreated for 24 h with 10 µM DWK-2 alone, or from DWK-2 pretreated cells and infected with ZIKV for 48 h was analyzed by qRT-PCR for the expression of ZIKV and GAPDH RNA. Results are shown in FIG. 15B. Relative expression of intracellular ZIKV RNA normalized to GAPDH RNA is reduced by 94.2%. Quantitation of ZIKV genome copy number in total intracellular RNA shows a reduction in ZIKV copy number in infected cells pretreated with DWK-2. Values represent mean±SD of 3 independent samples. ND, not detected.

H. Working Example 4

The toxicity of DWK-1 in mice was determined. DWK-1 toxicity data shown in CD-1 mice was performed by Pacific Biolab, Hercules Calif. (FIG. 7). A summary of the data that includes animal grouping, dosing regimen and mortality 96 h after s.c. injection is shown. All animals survived the highest dose of 30 mg/kg after temporary vasodilation and hypoactivity immediately after the dose. All groups recovered from temporary vasodilation and hypoactivity within 3 hours, with only a scruffy appearance and slight vasodilation. These data indicate that DWK-1 is non-toxic in CD-1 mice and support testing DWK-1 in a murine model for ZIKV infection.

I. Prophetic Example 5

DWK-1 dosing and toxicity in the murine model prior to ZIKV exposure. Multiple dosing of DWK-1 will be performed over a period 96 hours in CD-1 mice. The experiment will also be performed in pregnant female mice with the intention to examine ill effects of DWK-1 on the mother and pups. Multiple dosing (1 dose per day for 4 days) in 50 µl volumes will be administered intraperitoneally (i.p.). Animals will be examined daily for ill effects and pups will be examine after birth for toxicity and evidence of pathology. ZIKV infection of the murine model. Animals: Utilizing a predetermined dosing regimen for DWK-1 from previous toxicity studies an efficacy evaluation will be performed of DWK-1 in the ZIKV infected murine model previously described (Miner J J, Sene A, Richner J M, Smith A M, Santeford A, Ban N, Weger-Lucarelli J, Manzella F, Ruckert C, Govero J, Noguchi K K, Ebel G D, Diamond M S, Apte R S. Zika Virus Infection in Mice Causes Panuveitis with Shedding of Virus in Tears. Cell Rep. 2016; 20; 16(12):3208-3218). Animal studies in the ZIKV murine model will be performed as a fee for service with Washington University at St. Louis. All protocols will be approved by the Institutional Animal Care and Use Committee at the Washington University School of Medicine. Wild type C57BL/6 mice (Jackson Laboratories) will be treated with 2 mg of an anti-Ifnar1 blocking mouse MAb (MAR1-5A3) or isotype control mouse MAb (GIR-208) (Leinco Technologies). Virus: The ZIKV strain H/PF/2013 (French Polynesia) and the ZIKV PRVABC59 will be used in this study. ZIKV infections: Four to eight-week-old anti-Ifnar1 mice will be inoculated with ZIKV by the subcutaneous (footpad) route with 103 FFU in 50 µl of PBS and control animals will be given PBS only. Evaluation of ZIKV infected Mice: Mice will be examined daily for evidence of disease and pathology. Harvested organs will be examined for ZIKV infection by qRT-PCR. Evaluation of Animals Post Treatment: Treated and control mice infected with ZIKV will be examined for evidence of protection against ocular disease, systemic infection, and maternal transmission. In addition, animals will be assessed for toxicity, off target effects, viral loads in tissue and body fluids by qRT-PCR. Histological examinations of tissue will be done by immunohistochemistry (IHC).

Analysis of ZIKV infectivity in ocular tissue. Ocular tissue including the complete orbits of both the left and right eye of control and ZIKV infected mice with and without DWK-1 treatment will be processed separately as fresh frozen tissue (FFT) that will be stored in liquid nitrogen as well as formalin fix and paraffin embedded (FFPE) tissue. FFPE tissue will be laced on Chemate slides and H&E stained to examine gross pathology. Infected and control specimens will be stained by IHC for ZIKV infection using the 4G2 antibody. FFT will be analyzed for ZIKV RNA by qRT-PCR. Tears and lacrimal glands from infected and control animals will be examined for viral burden by qRT-PCR.

Analysis of ZIKV infectivity in pregnant mice treated with DWK-1 to prevent ZIKV induced ocular disease in pups. The vertical transmission of ZIKV in humans and the development of ocular disease in infants is well documented but the underlying mechanisms are poorly understood. Therapeutic modalities to prevent intrauterine transmission of ZIKV are currently not available. The ability of DWK-1 will be examined to prevent intrauterine transmission of ZIKV to pups and to prevent ZIKV associated CNS disease. Pregnant mice at the same gestational time point will be infected with ZIKV followed by a repeated subcutaneous dose of 20 mg/kg of DWK-1. This dose will be repeated daily for 5 days. Animals will be allowed to give birth and mother and pups will be examined for evidence of toxicity and ZIKV induced CNS pathology. Clinical and translational goals. Findings from the proposed studies will be utilized as a basis for evaluating DWK-1 in a macaque model with future implications for Phase I testing in humans.

J. Examplary Embodiments

Embodiment 1: An antiviral agent that restricts the replication of Zika virus (ZIKV) in a cell, the agent comprising a phosphorodiamidate morpholino oligomer (PMO) comprising an antisense sequence to a portion of a genome of a strain of ZIKV.

Embodiment 2: A pharmaceutical composition for the treatment or prevention of a disease mediated by the Zika virus (ZIKV), the composition comprising: the antiviral agent of embodiment 1 and a pharmaceutically acceptable carrier.

Embodiment 3: The pharmaceutical composition of embodiment 2, wherein the pharmaceutically acceptable carrier is selected from the group consisting of: a vehicle, an adjuvant, a surfactant, a suspending agent, an emulsifying agent, an inert filler, a diluent, an excipient, a wetting agent, a binder, a lubricant, a buffering agent, a disintegrating agent, an accessory agent, a coloring agent, and a flavoring agent.

Embodiment 4: The pharmaceutical composition of any one of embodiments 2-3, wherein the antiviral agent is present in a therapeutically effective amount.

Embodiment 5: The pharmaceutical composition of any one of embodiments 3-4, wherein the therapeutically effective amount is sufficient to provide the agent at a concentration of at least about 10 µM at a site of viral infection in a subject.

Embodiment 6: The pharmaceutical composition of any one of embodiments 3-5, wherein the therapeutically effective amount is a non-toxic amount.

Embodiment 7: The pharmaceutical composition of any one of embodiments 3-6, wherein the therapeutically effective amount is sufficient to provide the agent at a concentration of below an LD50 for a subject.

Embodiment 8: The pharmaceutical composition of any one of embodiments 3-7, wherein the therapeutically effective amount is sufficient to provide the agent at a dosage/body mass concentration of up to an amount selected from: 0.05, 0.1, 0.15, 0.2, 0.3, 0.5, 1, 1.5, 2, 3, 5, 10, 15, 20, 30 mg/kg, about any of the foregoing values, and a range between any of the foregoing values.

Embodiment 9: The pharmaceutical composition of any one of embodiments 2-8, wherein the pharmaceutical composition is formulated to deliver the antiviral agent to a subject's circulatory system, placenta, fetus, eye, kidney, brain, skin, or any combination of the foregoing.

Embodiment 10: A method of treatment or prevention of a disease mediated by the Zika virus (ZIKV) in a subject in need thereof, the method comprising administering to the subject a therapeutically effective amount of the pharmaceutical composition of any one of embodiments 2-9.

Embodiment 11: The composition or method of any one of embodiments 2-10, wherein the disease mediated by ZIKV is selected from the following group: Zika fever, Guillain-Barré syndrome, a congenital defect, microcephaly, ocular disease, and Zika associated organ pathology.

Embodiment 12: A method of reducing or preventing the replication of Zika virus (ZIKV) in a host cell, the method comprising contacting the host cell with an effective amount of the antiviral agent of embodiment 1.

Embodiment 13: The method of embodiment 12, wherein the host cell is selected from the group consisting of: a retinal endothelial cell, a retinal microvascular endothelial cell, a retinal pigmented epithelial cell, a retinal pericyte, a kidney cell, a glomerular podocyte, a renal glomerular endothelial cell, mesangial cell, cytotrophoblasts, syncytiotrophoblast, human brain microvascular endothelial cells, human neural stem cells, astrocytes, neuroblastoma cells, neural progenitor cells, placental endothelial cells, placental fibroblasts, Hofbauer cells, amniotic epithelial cells, chorionic villi cells, keratinocytes, dermal fibroblasts, dendritic cells, umbilical vein endothelial cells, aortic endothelial cells, coronary artery endothelial cells, saphenous vein endothelial cells, glial cells, primary spermatocytes, Sertoli cells, retinal bipolar cells, retinal ganglion cells, optic nerve cells, Vero cells, and combinations thereof.

Embodiment 14: A method of controlling the spread of ZIKV in a specimen of donated tissue or organ, the method comprising exposing the specimen to an effective amount of the antiviral agent of embodiment 1.

Embodiment 15: The method of embodiment 14, wherein the donated organ is selected from the group consisting of: heart, intestine, kidney, liver, lung, and pancreas; or the donated tissue is selected from the group consisting of: bone, cartilage, cornea, dura matter, fascia, heart valve, ligament, pericardium, skin, tendon, and vein.

Embodiment 16: The method of any one of embodiments 14-15, comprising perfusing the specimen with the antiviral agent.

Embodiment 17: The method of any one of embodiments 14-16, wherein the effective amount is at least about 10 µM.

Embodiment 18: The method of any one of embodiments 14-17, wherein the effective amount is a nontoxic amount.

Embodiment 19: A treated specimen of donated tissue or organ that is the product of the process of any one of embodiments 14-18.

Embodiment 20: Any one of embodiments 1-19, wherein the portion of the genome of the strain of ZIKV is a 5' portion comprising the untranslated region and the capsid protein.

Embodiment 21: Any one of embodiments 1-20, wherein the antisense sequence has at least 80% identity with 5'-CAT GAC CAG AAA CTC TCG TTT CCA A-3' (SEQ ID NO: 3).

Embodiment 22: Any one of embodiments 1-21, wherein the antisense sequence has at least a level of identity with 5'-CAT GAC CAG AAA CTC TCG TTT CCA A-3' (SEQ ID NO: 3) selected from the group consisting of: 85%, 90%, 95%, 99%, and 100%.

Embodiment 23: Any one of embodiments 1-22, wherein the antisense sequence hybridizes under physiological conditions with RNA containing the sequence 5'-TTG GAA ACG AGA GTT TCT GGT CAT G-3' (SEQ ID NO: 2).

Embodiment 24: Any one of embodiments 1-23, wherein the antisense sequence hybridizes under highly stringent conditions with RNA containing the sequence 5'-TTG GAA ACG AGA GTT TCT GGT CAT G-3' (SEQ ID NO: 2).

Embodiment 25: Any one of embodiments 1-19, wherein the portion of the genome of the strain of ZIKV is a 3' portion comprising the untranslated region.

Embodiment 26: Any one of embodiments 1-19, wherein the portion of the genome of the strain of ZIKV is a structure in the 3' portion comprising the untranslated region selected from the group consisting of: a stem-and-loop structure, and a short hairpin structure.

Embodiment 27: Any one of embodiments 1-19, wherein the portion of the genome of the strain of ZIKV is a structure in the 3' portion comprising the untranslated region selected from the group consisting of: SL I, SL II, SL I, sHP, and the terminal 3' end stem-and-loop structure.

Embodiment 28: Any one of embodiments 1-19 and 25-27, wherein the antisense sequence has at least 80% identity with 5'-CAT GGA GTC TCT GGT CTT TCC CAG C-3' (SEQ ID NO: 5).

Embodiment 29: Any one of embodiments 1-19 and 25-28, wherein the antisense sequence has at least a level of identity with 5'-CAT GGA GTC TCT GGT CTT TCC CAG C-3' (SEQ ID NO: 5) selected from the group consisting of: 85%, 90%, 95%, 99%, and 100%.

Embodiment 30: Any one of embodiments 1-19 and 25-29, wherein the antisense sequence hybridizes under physiological conditions with RNA containing the sequence 5'-GCT GGG AAA GAC CAG AGA CTC CAT G-3' (SEQ ID NO: 4).

Embodiment 31: Any one of embodiments 1-19 and 25-30, wherein the antisense sequence hybridizes under highly stringent conditions with RNA containing the sequence 5'-GCT GGG AAA GAC CAG AGA CTC CAT G-3' (SEQ ID NO: 4).

Embodiment 32: Any of embodiments 1-31, wherein the agent comprises a moiety for intracellular delivery.

Embodiment 33: Any of embodiments 1-32, wherein the agent comprises an octa-guanidine dendrimer delivery moiety.

Embodiment 34: Any of embodiments 1-33, wherein the agent comprises an octa-guanidine dendrimer of the following structure:

Embodiment 35: A use of the agent of any of embodiments 1 and 20-34 for the manufacture of a medicament for the treatment or prevention of a disease mediated by the Zika virus (ZIKV).

Embodiment 36: The use of embodiment 35, wherein the disease mediated by ZIKV is selected from the following group: Zika fever, Guillain-Barré syndrome, a congenital defect, microcephaly, ocular disease, and Zika associated organ pathology.

Embodiment 37: A use of the agent of any of embodiments 1 and 20-34 for the manufacture of a composition for controlling the spread of ZIKV in a specimen of donated tissue or organ.

K. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

We claim:

1. An antiviral agent that restricts the replication of Zika virus (ZIKV) in a cell, the agent comprising a phosphorodiamidate morpholino oligomer (PMO) comprising a sequence of 5'-CAT GAC CAG AAA CTC TCG TTT CCA A-3' (SEO ID NO: 3) or 5'-CAT GGA GTC TCT GGT CTT TCC CAG C-3' (SEQ ID NO: 5).

2. A pharmaceutical composition for the treatment or prevention of a disease mediated by the Zika virus (ZIKV), the composition comprising: the antiviral agent of claim 1 and a pharmaceutically acceptable carrier.

3. The pharmaceutical composition of claim 2, wherein the antiviral agent is present in a therapeutically effective amount.

4. The pharmaceutical composition of claim 3, wherein the therapeutically effective amount is sufficient to provide the agent at a concentration of at least about 10 μM at a site of viral infection in a subject.

5. The pharmaceutical composition of claim 3, wherein the therapeutically effective amount is a nontoxic amount.

6. The pharmaceutical composition of claim 3, wherein the therapeutically effective amount is sufficient to provide the agent at a dosage/body mass concentration of up to an amount selected from: 0.05, 0.1, 0.15, 0.2, 0.3, 0.5, 1, 1.5, 2, 3, 5, 10, 15, 20, 30 mg/kg, about any of the foregoing values, and a range between any of the foregoing values.

7. The pharmaceutical composition of claim 2, wherein the pharmaceutical composition is formulated to deliver the antiviral agent to: a circulatory system, a placenta, a fetus, an eye, a kidney, a brain, a skin, one or more testes, one or more neurons, one or more stem cells, a vagina, a spleen, an auditory system, or any combination of the foregoing, of a subject.

8. A method of treatment or prevention of a disease mediated by the Zika virus (ZIKV) in a subject in need thereof, the method comprising administering to the subject a therapeutically effective amount of the pharmaceutical composition of claim 2.

9. The antiviral agent of claim 1, wherein when the sequence comprises 5'-CAT GAC CAG AAA CTC TCG TTT CCA A-3' (SEQ ID NO: 3), the antiviral agent targets a sequence in the 5' region of the ZIKV virus.

10. The antiviral agent of claim 1, wherein when the sequence comprises 5'-CAT GAC CAG AAA CTC TCG TTT CCA A-3' (SEO ID NO: 3), the sequence hybridizes under physiological conditions with RNA containing the sequence 5'-TTG GAA ACG AGA GTT TCT GGT CAT G-3' (SEQ ID NO: 2).

11. The antiviral agent of claim 1, wherein when the sequence comprises 5'-CAT GGA GTC TCT GGT CTT TCC CAG C-3' (SEQ ID NO: 5), the antiviral agent targets a sequence in the 3' region of the ZIKV virus.

12. The antiviral agent of claim 1, wherein when the sequence comprises 5'-CAT GGA GTC TCT GGT CTT TCC CAG C-3' (SEQ ID NO: 5) the sequence hybridizes under physiological conditions with RNA containing the sequence 5'-GCT GGG AAA GAC CAG AGA CTC CAT G-3' (SEQ ID NO: 4).

13. The antiviral agent of claim 1, wherein the agent comprises a moiety for intracellular delivery.

14. The antiviral agent of claim 1, wherein the agent comprises an octa-guanidine dendrimer delivery moiety.

15. The antiviral agent of claim 1, wherein the agent comprises an octa-guanidine dendrimer of the following structure:

16. The pharmaceutical composition of claim 2, wherein the disease mediated by ZIKV is selected from the group consisting of: Zika fever, Guillain-Barre syndrome, a congenital defect, microcephaly, ocular disease, and Zika associated organ pathology.

17. The pharmaceutical composition of claim 3, wherein the therapeutically effective amount is sufficient to provide the agent at a concentration of below an LD50 for a subject.

18. The antiviral agent of claim 9, wherein the 5' region of the ZIKV virus comprises a 5' untranslated region.

19. The antiviral agent of claim 11 wherein the 3' region of the ZIKV virus comprises a 3' untranslated region.

20. The antiviral agent of claim 11, wherein the 3' region of the ZIKV virus comprises a 3' short hairpin structure.

* * * * *

SEQUENCE LISTING

```
<160> NUMBER OF SEQ ID NOS: 25

<210> SEQ ID NO 1
<211> LENGTH: 10794
<212> TYPE: DNA
<213> ORGANISM: Zika virus strain MR 766

<400> SEQUENCE: 1
agttgttgat ctgtgtgagt cagactgcga cagttcgagt ctgaagcgag agctaacaac      60
agtatcaaca ggtttaattt ggatttggaa acgagagttt ctggtcatga aaaaccccaa     120
agaagaaatc cggaggatcc ggattgtcaa tatgctaaaa cgcggagtag cccgtgtaaa    180
ccccttggga ggtttgaaga ggttgccagc cggacttctg ctgggtcatg gacccatcag    240
aatggttttg gcgatactag cctttttgag atttacagca atcaagccat cactgggcct    300
tatcaacaga tggggttccg tggggaaaaa agaggctatg gaaataataa agaagttcaa    360
gaaagatctt gctgccatgt tgagaataat caatgctagg aaagagagga agagacgtgg    420
cgcagacacc agcatcggaa tcattggcct cctgctgact acagccatgg cagcagagat    480
cactagacgc gggagtgcat actacatgta cttggatagg agcgatgccg ggaaggccat    540
ttcgtttgct accacattgg gagtgaacaa gtgccacgta cagatcatgg acctcgggca    600
catgtgtgac gccaccatga gttatgagtg ccctatgctg gatgagggag tggaaccaga    660
tgatgtcgat tgctggtgca acacgacatc aacttgggtt gtgtacggaa cctgtcatca    720 caaaaaggt gaggcacggc gatctagaag agccgtgacg ctcccttctc actctacaag    780
gaagttgcaa acgcggtcgc agacctggtt agaatcaaga gaatacacga agcacttgat    840
caaggttgaa aactggatat tcaggaaccc cgggtttgcg ctagtggccg ttgccattgc    900
ctggcttttg ggaagctcga cgagccaaaa agtcatatac ttggtcatga tactgctgat    960
tgccccggca tacagtatca ggtgcattgg agtcagcaat agagacttcg tggagggcat   1020
gtcaggtggg acctgggttg atgttgtctt ggaacatgga ggctgcgtta ccgtgatggc   1080
acaggacaag ccaacagtcg catagagtt ggtcacgacg acggttagta acatggccga   1140
ggtaagatcc tattgctacg aggcatcgat atcggacatg gcttcggaca gtcgttgccc   1200
aacacaaggt gaagcctacc ttgacaagca atcagacact caatatgtct gcaaaagaac   1260
attagtggac agaggttggg gaaacggttg tggactttt ggcaaaggga gcttggtgac   1320
atgtgccaag tttacgtgtt ctaagaagat gaccgggaag agcattcaac cggaaaatct   1380
ggagtatcgg ataatgctat cagtgcatgg ctcccagcat agcgggatga ttggatatga   1440
aactgacgaa gatagagcga aagtcgaggt tacgcctaat tcaccaagag cggaagcaac   1500
cttgggaggc tttggaagct taggacttga ctgtgaacca aggacaggcc ttgactttc   1560 agatctgtat tacctgacca tgaacaataa gcattggttg gtgcacaaag agtggtttca   1620
tgacatccca ttgccttggc atgctggggc agacaccgga actccacact ggaacaacaa   1680
agaggcattg gtagaattca aggatgccca cgccaagagg caaaccgtcg tcgttctggg   1740
gagccaggaa ggagccgttc acacggctct cgctggagct ctagaggctg agatggatgg   1800
tgcaaaggga aggctgttct ctggccattt gaaatgccgc ctaaaaatgg acaagcttag   1860
```

-continued

```
attgaagggc gtgtcatatt ccttgtgcac tgcggcattc acattcacca aggtcccagc    1920
tgaaacactg catggaacag tcacagtgga ggtgcagtat gcagggacag atggaccctg    1980
caagatccca gtccagatgg cggtggacat gcagaccctg accccagttg aaggctgat     2040
aaccgccaac cccgtgatta ctgaaagcac tgagaactca agatgatgt tggagcttga     2100
cccaccattt ggggattctt acattgtcat aggagttggg gacaagaaaa tcacccacca    2160
ctggcatagg agtggtagca ccatcggaaa ggcatttgag gccactgtga gaggcgccaa    2220
gagaatggca gtcctggggg atacagcctg gacttcgga tcagtcgggg gtgtgttcaa     2280
ctcactgggt aagggcattc accagatttt tggagcagcc ttcaaatcac tgtttggagg    2340
aatgtcctgg ttctcacaga tcctcatagg cacgctgcta gtgtggttag gtttgaacac    2400
aaagaatgga tctatctccc tcacatgctt ggccctgggg ggagtgatga tcttcctctc    2460
cacggctgtt tctgctgacg tggggtgctc agtggacttc tcaaaaaagg aaacgagatg    2520
tggcacgggg gtattcatct ataatgatgt tgaagcctgg agggaccggt acaagtacca    2580
tcctgactcc ccccgcagat tggcagcagc agtcaagcag gctgggaag aggggatctg    2640
tgggatctca tccgtttcaa gaatggaaaa catcatgtgg aaatcagtag aagggagct     2700
caatgctatc ctagaggaga atggagttca actgacagtt gttgtgggat ctgtaaaaaa    2760
ccccatgtgg agaggtccac aaagattgcc agtgcctgtg aatgagctgc cccatggctg    2820
gaaagcctgg gggaaatcgt attttgttag ggcggcaaag accaacaaca gttttgttgt    2880
cgacggtgac acactgaagg aatgtccgct tgagcacaga gcatggaata gttttcttgt    2940
ggaggatcac gggtttggag tcttccacac cagtgtctgg cttaaggtca gagaagatta    3000
ctcattagaa tgtgacccag ccgtcatagg aacagctgtt aagggaaggg aggccgcgca    3060
cagtgatctg ggctattgga ttgaaagtga aagaatgac acatggaggc tgaagagggc     3120
ccacctgatt gagatgaaaa catgtgaatg ccaaagtct cacacattgt ggacagatgg    3180
agtagaagaa agtgatctta tcatacccaa gtctttagct ggtccactca gccaccacaa    3240
caccagagag ggttacagaa cccaagtgaa agggccatgg cacagtgaag agcttgaaat    3300
ccggtttgag gaatgtccag gcaccaaggt ttacgtggag gagacatgcg gaactagagg    3360
accatctctg agatcaacta ctgcaagtgg aagggtcatt gaggaatggt gctgtaggga    3420
atgcacaatg cccccactat cgtttcgagc aaaagacggc tgctggtatg gaatggagat    3480
aaggcccagg aaagaaccag agagcaactt agtgaggtca atggtgacag cggggtcaac    3540
cgatcatatg gaccacttct ctcttggagt gcttgtgatt ctactcatgg tgcaggaggg    3600
gttgaagaag agaatgacca caaagatcat catgagcaca tcaatggcag tgctggtagt    3660
catgatcttg ggaggatttt caatgagtga cctggccaag cttgtgatcc tgatgggtgc    3720
tactttcgca gaaatgaaca ctggaggaga tgtagctcac ttggcattgg tagcggcatt    3780
taaagtcaga ccagccttgc tggtctcctt cattttcaga gccaattgga cacccgtga     3840
gagcatgctg ctagccctgg cttcgtgtct tctgcaaact gcgatctctg ctcttgaagg    3900
tgacttgatg gtcctcatta atggatttgc tttggcctgg ttggcaattc gagcaatggc    3960
cgtgccacgc actgacaaca tcgctctacc aatcttggct gctctaacac cactagctcg    4020
aggcacactg ctcgtggcat ggagagcggg cctggctact tgtggaggga tcatgctcct    4080
ctccctgaaa gggaaggta gtgtgaagaa gaacctgcca tttgtcatgg ccctgggatt    4140
gacagctgtg agggtagtag acccctattaa tgtggtagga ctactgttac tcacaaggag    4200
tgggaagcgg agctggcccc ctagtgaagt tctcacagcc gttggcctga tatgtgcact    4260
```

```
ggccggaggg tttgccaagg cagacattga gatggctgga cccatggctg cagtaggctt      4320
gctaattgtc agctatgtgg tctcgggaaa gagtgtggac atgtacattg aaagagcagg      4380
tgacatcaca tgggaaaagg acgcggaagt cactggaaac agtcctcggc ttgacgtggc      4440
actggatgag agtggtgact tctccttggt agaggaagat ggtccaccca tgagagagat      4500
catactcaag gtggtcctga tggccatctg tggcatgaac ccaatagcta tacctttgc       4560 tgcaggagcg tggtatgtgt atgtgaagac tgggaaaagg agtggcgccc tctgggacgt      4620
gcctgctccc aaagaagtga agaaaggaga gaccacagat ggagtgtaca gagtgatgac      4680
tcgcagactg ctaggttcaa cacaggttgg agtgggagtc atgcaagagg gagtcttcca      4740
caccatgtgg cacgttacaa aaggagccgc actgaggagc ggtgagggaa gacttgatcc      4800
atactggggg gatgtcaagc aggacttggt gtcatactgt gggccttgga agttggatgc      4860
agcttgggat ggactcagcg aggtacagct tttggccgta cctcccggag agagggccag      4920
aaacattcag accctgcctg gaatattcaa gacaaaggac ggggacatcg gagcagttgc      4980
tctggactac cctgcaggga cctcaggatc tccgatccta gacaaatgtg gaagagtgat      5040
aggactctat ggcaatgggg ttgtgatcaa gaatggaagc tatgttagtg ctataaccca      5100
gggaaagagg gaggaggaga ctccggttga atgtttcgaa ccctcgatgc tgaagaagaa      5160
gcagctaact gtcttggatc tgcatccagg agccggaaaa accaggagag ttcttcctga      5220
aatagtccgt gaagccataa aaagagact ccggacagtg atcttggcac caactagggt       5280
tgtcgctgct gagatggagg aggccttgag aggacttccg gtgcgttaca tgacaacagc      5340
agtcaacgtc acccattctg ggacagaaat cgttgatttg atgtgccatg ccactttcac      5400
ttcacgctta ctacaaccca tcagagtccc taattacaat ctcaacatca tggatgaagc      5460
ccacttcaca gaccctcaa gtatagctgc aagaggatac atatcaacaa gggttgaaat        5520
gggcgaggcg gctgccattt tatgactgc cacaccacca ggaacccgtg atgcgtttcc        5580
tgactctaac tcaccaatca tggacacaga agtggaagtc ccagagagag cctggagctc      5640
aggctttgat tgggtgacag accattctgg gaaaacagtt tggttcgttc aagcgtgag       5700 aaacggaaat gaaatcgcag cctgtctgac aaaggctgga aagcgggtca tacagctcag      5760
caggaagact tttgagacag aatttcagaa aacaaaaaat caagagtggg actttgtcat      5820
aacaactgac atctcagaga tgggcgccaa cttcaaggct gaccgggtca tagactctag      5880
gagatgccta aaaccagtca tacttgatgg tgagagagtc atcttggctg ggcccatgcc      5940
tgtcacgcat gctagtgctg ctcagaggag aggacgtata ggcaggaacc ctaacaaacc      6000
tggagatgag tacatgtatg gaggtgggtg tgcagagact gatgaaggcc atgcacactg      6060
gcttgaagca agaatgcttc ttgacaacat ctacctccag gatggcctca gcctcgct       6120 ctatcggcct gaggccgata aggtagccgc cattgaggga gagtttaagc tgaggacaga      6180
gcaaaggaag accttcgtgg aactcatgaa gagaggagac cttcccgtct ggctagccta      6240
tcaggttgca tctgccggaa taacttacac agacagaaga tggtgctttg atggcacaac      6300
caacaacacc ataatggaag acagtgtacc agcagaggtt tggacaaagt atggagagaa      6360
gagagtgctc aaaccgagat ggatggatgc tagggtctgt tcagaccatg cggccctgaa      6420
gtcgttcaaa gaattcgccg ctggaaaaag aggagcggct ttgggagtaa tggaggccct      6480
gggaacactg ccaggacaca tgacagagag gtttcaggaa gccattgaca acctcgccgt      6540
gctcatgcga gcagagactg gaagcaggcc ttataaggca gcggcagccc aactgccgga      6600
gaccctagag accattatgc tcttaggttt gctgggaaca gtttcactgg ggatcttctt      6660
```

```
cgtcttgatg cggaataagg gcatcgggaa gatgggcttt ggaatggtaa cccttggggc    6720
cagtgcatgg ctcatgtggc tttcggaaat tgaaccagcc agaattgcat gtgtcctcat    6780
tgttgtgttt ttattactgg tggtgctcat acccgagcca gagaagcaaa gatctcccca    6840
agataaccag atggcaatta tcatcatggt ggcagtgggc cttctaggtt tgataactgc    6900
aaacgaactt ggatggctgg aaagaacaaa aaatgacata gctcatctaa tgggaaggag    6960
agaagaagga gcaaccatgg gattctcaat ggacattgat ctgcggccag cctccgcctg    7020
ggctatctat gccgcattga caactctcat caccccagct gtccaacatg cggtaaccac    7080
ttcatacaac aactactcct taatggcgat ggccacacaa gctggagtgc tgtttggcat    7140
gggcaaaggg atgccattta tgcatgggga ccttggagtc ccgctgctaa tgatgggttg    7200
ctattcacaa ttaacacccc tgactctgat agtagctatc attctgcttg tggcgcacta    7260
catgtacttg atcccaggcc tacaagcggc agcagcgcgt gctgcccaga aaggacagc    7320 agctggcatc atgaagaatc cgttgtggga tggaatagtg gtaactgaca ttgacacaat    7380
gacaatagac ccccaggtgg agaagaagat gggacaagtg ttactcatag cagtagccat    7440
ctccagtgct gtgctgctgc ggaccgcctg gggatggggg gaggctggag ctctgatcac    7500
agcagcgacc tccaccttgt gggaaggctc tccaaacaaa tactgaaact cctctacagc    7560
caactcactg tgcaacatct tcagaggaag ctatctggca ggagcttccc ttatctatac    7620
agtgacgaga aacgctggcc tggttaagag acgtggaggt gggacgggag agactctggg    7680
agagaagtgg aaagctcgtc tgaatcagat gtcggccctg gagttctact cttataaaaa    7740
gtcaggtatc actgaagtgt gtagagagga ggctcgccgt gccctcaagg atggagtggc    7800
cacaggagga catgccgtat cccggggaag tgcaaagatc agatggttgg aggagagagg    7860
atatctgcag ccctatggga aggttgttga cctcggatgt ggcagagggg gctgagcta    7920 ttatgccgcc accatccgca aagtgcagga ggtgagagga tacacaaagg gaggtcccgg    7980
tcatgaagaa cccatgctgg tgcaaagcta tgggtggaac atagttcgtc tcaagagtgg    8040
agtggacgtc ttccacatgg cggctgagcc gtgtgacact ctgctgtgtg acataggtga    8100
gtcatcatct agtcctgaag tggaagagac acgaacactc agagtgctct ctatggtggg    8160
ggactggctt gaaaaaagac caggggcctt ctgtataaag gtgctgtgcc catacaccag    8220
cactatgatg gaaaccatgg agcgactgca acgtaggcat gggggaggat tagtcagagt    8280
gccattgtgt cgcaactcca cacatgagat gtactgggtc tctggggcaa agagcaacat    8340
cataaaaagt gtgtccacca caagtcagct cctcctggga cgcatggatg gccccaggag    8400
gccagtgaaa tatgaggagg atgtgaacct cggctcgggt acacgagctg tgcaagctg    8460 tgctgaggct cctaacatga aaatcatcgg caggcgcatt gagagaatcc gcaatgaaca    8520
tgcagaaaca tggttcttg atgaaaacca cccatacagg acatgggcct accatgggag    8580
ctacgaagcc cccacgcaag gatcagcgtc ttccctcgtg aacggggttg ttagactcct    8640
gtcaaagcct tgggacgtgg tgactggagt tacaggaata gccatgactg acaccacacc    8700
atacggccaa caaagagtct tcaaagaaaa agtggacacc agggtgccag atccccaaga    8760
aggcactcgc caggtaatga acatagtctc ttcctggctg tggaaggagc tggggaaacg    8820
caagcggcca cgcgtctgca ccaaagaaga gtttatcaac aaggtgcgca gcaatgcagc    8880
actgggagca atatttgaag aggaaaaaga atgaagacg gctgtggaag ctgtgaatga    8940
tccaaggttt tgggccctag tggatgggga gagaaacac cacctgagag gagagtgtca    9000
cagctgtgtg tacaacatga tgggaaaaag agaaaagaag caaggagagt tcgggaaagc    9060
```

-continued

```
aaaaggtagc cgcgccatct ggtacatgtg gttgggagcc agattcttgg agtttgaagc   9120
ccttggattc ttgaacgagg accattggat gggaagagaa aactcaggag gtggagtcga   9180
agggttagga ttgcaaagac ttggatacat tctagaagaa atgaatcggg caccaggagg   9240
aaagatgtac gcagatgaca ctgctggctg ggacacccgc attagtaagt ttgatctgga   9300
gaatgaagct ctgattacca accaaatgga ggaagggcac agaactctgg cgttggccgt   9360
gattaaatac acataccaaa acaaagtggt gaaggttctc agaccagctg aaggaggaaa   9420
aacagttatg gacatcattt caagacaaga ccagagaggg agtggacaag ttgtcactta   9480
tgctctcaac acattcacca acttggtggt gcagcttatc cggaacatgg aagctgagga   9540
agtgttagag atgcaagact tatggttgtt gaggaagcca gagaaagtga ccagatggtt   9600
gcagagcaat ggatgggata gactcaaacg aatggcggtc agtggagatg actgcgttgt   9660
gaagccaatc gatgataggt ttgcacatgc cctcaggttc ttgaatgaca tgggaaaagt   9720
taggaaagac acacaggagt ggaaaccctc gactggatgg agcaattggg aagaagtccc   9780
gttctgctcc caccacttca acaagctgta cctcaaggat gggagatcca ttgtggtccc   9840
ttgccgccac caagatgaac tgattggccg agctcgcgtc tcaccagggg caggatggag   9900
catccgggag actgcctgtc ttgcaaaatc atatgcgcag atgtggcagc tcctttattt   9960
ccacagaaga gaccttcgac tgatggctaa tgccatttgc tcggctgtgc cagttgactg  10020
ggtaccaact gggagaacca cctggtcaat ccatggaaag ggagaatgga tgaccactga  10080
ggacatgctc atggtgtgga atagagtgtg gattgaggag aacgaccata tggaggacaa  10140
gactcctgta acaaaatgga cagacattcc ctatctagga aaaagggagg acttatggtg  10200
tggatccctt atagggcaca gaccccgcac cacttgggct gaaaacatca aagacacagt  10260
caacatggtg cgcaggatca taggtgatga agaaaagtac atggactatc tatccaccca  10320
agtccgctac ttgggtgagg aagggtccac acccggagtg ttgtaagcac caattttagt  10380
gttgtcaggc ctgctagtca gccacagttt ggggaaagct gtgcagcctg taaccccccc  10440
aggagaagct gggaaaccaa gctcatagtc aggccgagaa cgccatggca cggaagaagc  10500
catgctgcct gtgagcccct cagaggacac tgagtcaaaa aaccccacgc gcttggaagc  10560
gcaggatggg aaaagaaggt ggcgaccttc cccacccttc aatctggggc ctgaactgga  10620
gactagctgt gaatctccag cagagggact agtggttaga ggagaccccc cggaaaacgc  10680
aaaacagcat attgacgtgg gaaagaccag agactccatg agtttccacc acgctggccg  10740
ccaggcacag atcgccgaac ttcggcggcc ggtgtgggga aatccatggt ttct        10794
```
<210> SEQ ID NO 2
<211> LENGTH: 25
<212> TYPE: DNA
<213> ORGANISM: Zika virus

<400> SEQUENCE: 2

```
ttggaaacga gagtttctgg tcatg                                          25
```

<210> SEQ ID NO 3
<211> LENGTH: 25
<212> TYPE: DNA
<213> ORGANISM: Artificial Sequence
<220> FEATURE:
<223> OTHER INFORMATION: phosphorodiamidate morpholino oligomer

<400> SEQUENCE: 3

```
catgaccaga aactctcgtt tccaa                                          25
```

<210> SEQ ID NO 4
<211> LENGTH: 25
<212> TYPE: DNA
<213> ORGANISM: Zika virus

<400> SEQUENCE: 4
gctgggaaag accagagact ccatg                                    25

<210> SEQ ID NO 5
<211> LENGTH: 25
<212> TYPE: DNA
<213> ORGANISM: artificial sequence
<220> FEATURE:
<223> OTHER INFORMATION: phosphorodiamidate morpholino oligomer

<400> SEQUENCE: 5
catggagtct ctggtctttc ccagc                                    25

<210> SEQ ID NO 6
<211> LENGTH: 25
<212> TYPE: DNA
<213> ORGANISM: artificial sequence
<220> FEATURE:
<223> OTHER INFORMATION: PCR primer

<400> SEQUENCE: 6
aggatcatag gtgatgaaga aaagt                                    25

<210> SEQ ID NO 7
<211> LENGTH: 23
<212> TYPE: DNA
<213> ORGANISM: artificial sequence
<220> FEATURE:
<223> OTHER INFORMATION: PCR primer

<400> SEQUENCE: 7
cctgacaaca ctaagattgg tgc                                      23

<210> SEQ ID NO 8
<211> LENGTH: 18
<212> TYPE: DNA
<213> ORGANISM: artificial sequence
<220> FEATURE:
<223> OTHER INFORMATION: PCR primer

<400> SEQUENCE: 8
gaaggtgaag gtcggagt                                            18

<210> SEQ ID NO 9
<211> LENGTH: 20
<212> TYPE: DNA
<213> ORGANISM: artificial sequence
<220> FEATURE:
<223> OTHER INFORMATION: PCR primer

<400> SEQUENCE: 9
gaagatggtg atgggatttc                                          20

<210> SEQ ID NO 10
<211> LENGTH: 71
<212> TYPE: DNA
<213> ORGANISM: Zika virus

-continued

<400> SEQUENCE: 10
gtatcaacag gttttatttt ggatttggaa acgagagttt ctggtcatga aaaacccaaa    60
aaagaaatcc g    71

<210> SEQ ID NO 11
<211> LENGTH: 25
<212> TYPE: DNA
<213> ORGANISM: artificial sequence
<220> FEATURE:
<223> OTHER INFORMATION: phosphorodiamidate morpholino oligomer

<400> SEQUENCE: 11
cctcttacct cagttacaat ttata    25

<210> SEQ ID NO 12
<211> LENGTH: 17
<212> TYPE: DNA
<213> ORGANISM: Zika virus

<400> SEQUENCE: 12
ccgctgccca acacaag    17

<210> SEQ ID NO 13
<211> LENGTH: 24
<212> TYPE: DNA
<213> ORGANISM: Zika virus

<400> SEQUENCE: 13
ccactaacgt tcttttgcag acat    24

<210> SEQ ID NO 14
<211> LENGTH: 24
<212> TYPE: DNA
<213> ORGANISM: artificial sequence
<220> FEATURE:
<223> OTHER INFORMATION: PCR primer

<400> SEQUENCE: 14
cttggattcc tacaaagaag cagc    24

<210> SEQ ID NO 15
<211> LENGTH: 22
<212> TYPE: DNA
<213> ORGANISM: artificial sequence
<220> FEATURE:
<223> OTHER INFORMATION: PCR primer

<400> SEQUENCE: 15
tcctccttct ggaactgctg ca    22

<210> SEQ ID NO 16
<211> LENGTH: 22
<212> TYPE: DNA
<213> ORGANISM: artificial sequence
<220> FEATURE:
<223> OTHER INFORMATION: PCR primer

<400> SEQUENCE: 16
cctgctgctt tgcctacatt gc    22

<210> SEQ ID NO 17
<211> LENGTH: 22
<212> TYPE: DNA
<213> ORGANISM: artificial sequence
<220> FEATURE:
<223> OTHER INFORMATION: PCR primer

<400> SEQUENCE: 17
acacacttgg cggttctttc gg                                          22

<210> SEQ ID NO 18
<211> LENGTH: 22
<212> TYPE: DNA
<213> ORGANISM: artificial sequence
<220> FEATURE:
<223> OTHER INFORMATION: PCR primer

<400> SEQUENCE: 18
actttgagac gagcagccag tg                                          22

<210> SEQ ID NO 19
<211> LENGTH: 22
<212> TYPE: DNA
<213> ORGANISM: artificial sequence
<220> FEATURE:
<223> OTHER INFORMATION: PCR primer

<400> SEQUENCE: 19
tttctggacc cactcctcac tg                                          22

<210> SEQ ID NO 20
<211> LENGTH: 22
<212> TYPE: DNA
<213> ORGANISM: artificial sequence
<220> FEATURE:
<223> OTHER INFORMATION: PCR primer

<400> SEQUENCE: 20
ctcttctgcc tgctgcactt tg                                          22

<210> SEQ ID NO 21
<211> LENGTH: 22
<212> TYPE: DNA
<213> ORGANISM: artificial sequence
<220> FEATURE:
<223> OTHER INFORMATION: PCR primer

<400> SEQUENCE: 21
atgggctaca ggcttgtcac tc                                          22

<210> SEQ ID NO 22
<211> LENGTH: 24
<212> TYPE: DNA
<213> ORGANISM: artificial sequence
<220> FEATURE:
<223> OTHER INFORMATION: PCR Primer

<400> SEQUENCE: 22
tgtatgtgac tgcccaagat gaag                                        24

<210> SEQ ID NO 23
<211> LENGTH: 22
<212> TYPE: DNA
<213> ORGANISM: artificial sequence
<220> FEATURE:
<223> OTHER INFORMATION: PCR primer

```
<400> SEQUENCE: 23
agaggaggtt ggtctcacta cc                                                22

<210> SEQ ID NO 24
<211> LENGTH: 22
<212> TYPE: DNA
<213> ORGANISM: artificial sequence
<220> FEATURE:
<223> OTHER INFORMATION: PCR primer

<400> SEQUENCE: 24
agacagccac tcacctcttc ag                                                22

<210> SEQ ID NO 25
<211> LENGTH: 22
<212> TYPE: DNA
<213> ORGANISM: artificial sequence
<220> FEATURE:
<223> OTHER INFORMATION: PCR primer

<400> SEQUENCE: 25
ttctgccagt gcctctttgc tg                                                22
```